United States Patent [19]

Cooke et al.

[11] Patent Number: 4,772,692
[45] Date of Patent: Sep. 20, 1988

[54] INTERMEDIATE COMPOUNDS FOR THE PREPARATION OF ANTIBACTERIAL PENEM DERIVATIVES

[75] Inventors: Michael D. Cooke, Newport Pagnell; Barry C. Ross, Luton, both of Great Britain

[73] Assignee: Hoechst UK Limited, Hounslow, Great Britain

[21] Appl. No.: 854,998

[22] Filed: Apr. 22, 1986

Related U.S. Application Data

[60] Division of Ser. No. 619,703, Jun. 14, 1984, Pat. No. 4,585,767, which is a continuation of Ser. No. 395,646, Jul. 6, 1982, abandoned.

[30] Foreign Application Priority Data

Jul. 8, 1981 [GB] United Kingdom ............... 8121108
Mar. 11, 1982 [GB] United Kingdom ............... 8207136

[51] Int. Cl.$^4$ ............... C07D 205/08; C07D 401/12; C07D 409/12; C07F 7/18
[52] U.S. Cl. .................................................. 540/360
[58] Field of Search ............... 260/239 A, 330.3; 546/275, 153, 155, 156, 157, 141, 142; 540/360

[56] References Cited

PUBLICATIONS

Ross, Chem Abs 101, 6934h (1984).

*Primary Examiner*—Mark L. Berch
*Attorney, Agent, or Firm*—Curtis, Morris & Safford

[57] ABSTRACT

Intermediate compounds of the formula

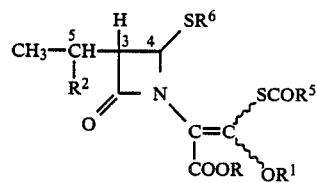

for the preparation of antibacterially active penem compounds and salts wherein R is hydrogen or an esterifying group, $R^1$ is an unsubstituted or a mono-, di-, or tri-substituted phenyl, naphthyl, thienyl, pyridyl, quinolyl or isoquinolyl, $R^2$ is hydrogen or a hydroxyl group which may be protected, $R^4$ is chlorine or bromine and $R^5$ is an alkyl or phenyl group; methods for making such compounds or salts.

5 Claims, No Drawings

INTERMEDIATE COMPOUNDS FOR THE PREPARATION OF ANTIBACTERIAL PENEM DERIVATIVES

This application is a division of application Ser. No. 619,703, filed June 14, 1984, now U.S. Pat. No. 4,585,767 dated Apr. 29, 1986, which is a continuation of Ser. No. 395,646, filed July 6, 1982, now abandoned.

This invention relates to penem derivatives, to a process for their preparation, to pharmaceutical preparations comprising them, and to intermediates for use in the preparation of substances having antibacterial activity and/or β-lactamase inhibitory and/or inactivating activity.

The term "penem" is used herein to denote the following structure

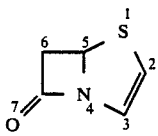

The present invention provides a compound of the general formula I

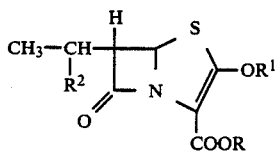

in which

R represents a hydrogen atom or a carboxyl esterifying group, $R^1$ represents a phenyl, naphthyl, thienyl, pyridyl, quinolyl or isoquinolyl group bonded at a ring carbon atom to the oxygen atom attached to the 2-position of the penem ring structure, a group $R^1$ being unsubstituted or substituted by one, two or three substituents, which may be the same or different, selected from halogen atoms and —OH, —$NH_2$, —$NO_2$, —CN, —$N_3$, $R^3$—, $R^3O$—, $R^3S$—, $R^3$—SO—, $R^3$—$SO_2$—, $R^3$—CO—, $R^3O$—CO—, $R^3$—CO—O—, $H_2N$—CO—,

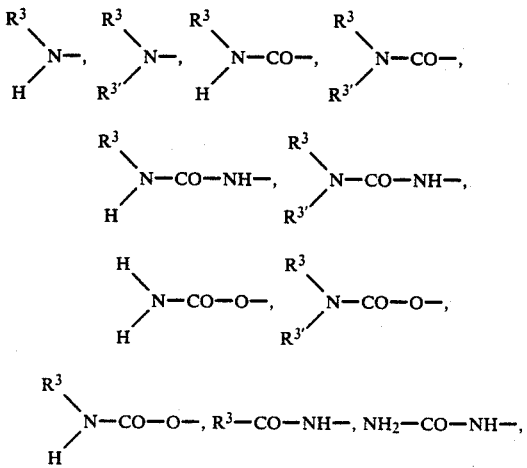

-continued
$R^3$—$SO_2$—NH—, $NH_2$—$SO_2$—NH—, $H_2N$—$SO_2$—,

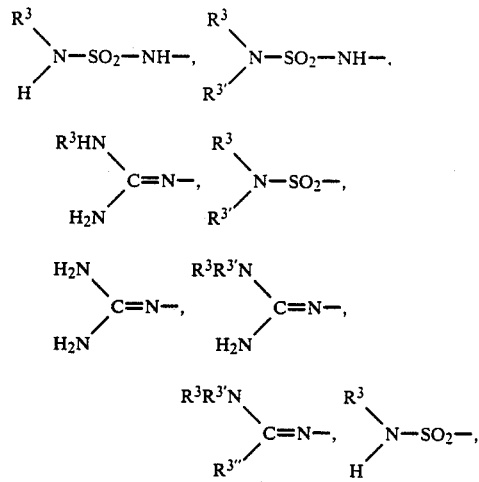

—$CF_3$, —$SCF_3$, $SCCF_3$, —$SO_2CF_3$ and HO—CO— groups, in which $R^3$, $R^{3'}$ and $R^{3''}$ each represents an alkyl group having from 1 to 4 carbon atoms, $R^3$, $R^{3'}$ and $R^{3''}$ being the same or different, and $R^2$ represents a hydrogen atom, or a hydroxyl group which may be protected by a hydroxyl protecting group.

The invention also provides salts of a compound of formula I, especially physiologically tolerable salts thereof.

The stereochemistry at positions 5, 6 and, when $R^2$ represents a hydroxyl group, at position 8, can be R or S independently (R and S being as defined by the Cahn-Ingold-Prelog system of nomenclature). The preferred stereo-chemistry at position 5 is R. When $R^2$ is a hydroxyl or protected hydroxyl group, the stereochemistry is preferably S at position 6 and R at position 8.

The invention further provides a process for the production of a compound of the general formula I or a salt thereof, which comprises reacting a compound of the general formula II

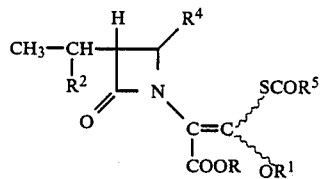

in which

R, $R^1$ and $R^2$ are as defined above $R^4$ represents a chlorine or bromine atom, and $R^5$ represents an alkyl group having from 1 to 4 carbon atoms, or a phenyl group, with a base, and, if desired, carrying out any one or more of the following steps in any desired order:

(a) converting an ester of formula I into the corresponding free acid, (b) converting a free acid of formula I into an ester thereof, (c) transesterifying a compound of formula I, (d) converting a free acid or an ester of formula I into a salt, or a salt into the free acid, an ester, or another salt, (e) removing any protective groups present other than an esterifying group R, (f) converting a substituent of a group $R^1$ into another substituent of $R^1$.

Protective groups for hydroxy groups are well known, and these and other protective groups are described below.

The term "lower" as used herein denotes a molecule, group or radical having up to 4 carbon atoms. Unless stated otherwise, halogen atoms are fluorine, chlorine, bromine and iodine atoms. The term "known" means in actual use in the art or described in the literature of the art.

$R^1$ may represent, for example, an unsubstituted phenyl group or a phenyl group substituted by a chlorine, fluorine, trifluoromethyl, methyl, methoxy, nitro, cyano, amino, methylthio, methylsulphinyl, methylsulphonyl, methylcarbonylamino, methylsulphonylamino or methylaminocarbonylamino group. $R^1$ may also represent a phenyl group substituted by more than one group, for example, by two or three methyl or methoxy groups. A heterocyclic group $R^1$ may also carry up to three substituents, for example, one or two methyl groups, preferably at ring carbon atoms.

It will be appreciated that the choice of substituents for $R^1$ may be subject to considerations of stereochemistry and also of possible interactions between the substituents themselves and other parts of a molecule in which $R^1$ is present, for example, $R^1$ may have 1, 2 or 3 substituents, but not more than one should be selected from (a) —OH and —$NH_2$ groups and not more than one should be selected from (b) —CN, —$NO_2$, $R^3$—CO—, $R^3O$—CO—, $R^3$—SO— and $R^3$—$SO_2$— groups. (Other substituents may, of couse, be present on $R^1$ in addition to a group selected from (a) and/or a group selected from (b).)

The expert will be aware of any restrictions on the choice of substituents, as such restrictions are known in the art.

An esterified carboxyl group —COOR is, for example, an ester formed with an unsubstituted or substituted aliphatic, cycloaliphatic, cycloaliphatic-aliphatic, aryl, araliphatic, heterocyclic or heterocyclic-aliphatic alcohol having up to 20 carbon atoms or is, for example, a silyl or stannyl ester.

An aliphatic group R is, for example a straight or branched chain substituted or unsubstituted alkyl, alkenyl or alkynyl group having up to 18 carbon atoms, preferably up to 8 carbon atoms, and especially up to 4 carbon atoms, for example, a methyl, ethyl, n-propyl, iso-propyl, n-butyl, sec-butyl, isobutyl, tert-butyl, n-pentyl, n-hexyl, allyl, or vinyl group.

An aliphatic group R, especially a methyl group, may be substituted by a cycloalkyl, aryl or heterocyclic group, for example, a pyridylmethyl groups, or R may itself represent a cycloalkyl, aryl or heterocyclic group.

A cycloaliphatic group R may have up to 18 carbon atoms and is, for example, a cyclopentyl, cyclohexyl or adamantyl group. An aryl group R may have up to 12 carbon atoms and may have two or more fused rings. An aryl group R is, for example, an unsubstituted or substituted phenyl group, and an unsubstituted or substituted aralkyl group is, for example, a benzyl, p-nitrobenzyl or benzhydryl group.

A heterocyclic group R may have one or more, preferably one to three, heteroatoms, which may be the same or different, selected from oxygen, nitrogen and sulphur, and up to 14 atoms in total. A heterocyclic group is, for example, an oxygen-containing heterocyclic group, for example, a tetrahydropyranyl or phthalidyl group.

A stannyl group R may have up to 24 carbon atoms, for example, R may represent a stannyl group having three substituents, which may be the same or different, selected from alkyl, alkenyl, cycloalkyl, aryl, aralkyl, alkoxy and aralkoxy groups, for example, alkyl groups having up to 4 carbon atoms, for example, n-butyl groups, phenyl and benzyl groups, especially three n-butyl groups.

A silyl group R has three substituents on the silicon atom and preferably up to 24 carbon atoms in total. The three substituents may be the same or different, and selected from alkyl, alkenyl, cycloalkyl, aryl and aralkyl groups, preferably selected from alkyl groups having up to 4 carbon atoms and phenyl groups, especially selected from methyl, t-butyl and phenyl groups. Preferred silyl groups are trimethylsilyl, diphenyl-t-butylsilyl, and dimethyl-t-butylsilyl groups.

Any group R that is capable of substitution may be substituted. Examples of substituents are halogen atoms;

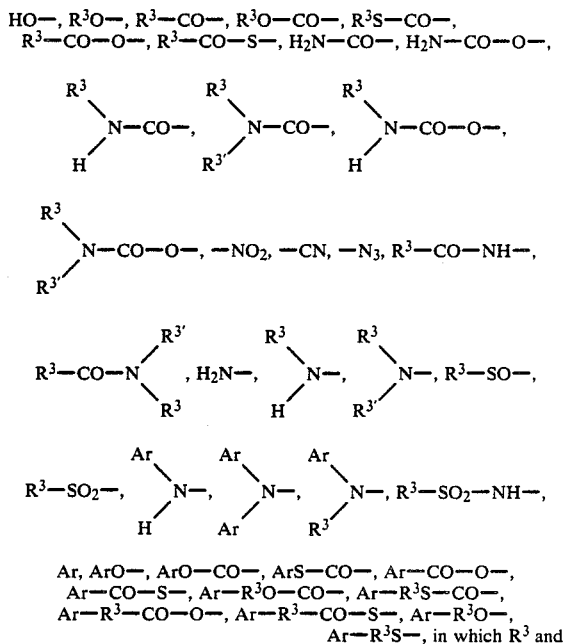

Ar, ArO—, ArO—CO—, ArS—CO—, Ar—CO—O—, Ar—CO—S—, Ar—$R^3$O—CO—, Ar—$R^3$S—CO—, Ar—$R^3$—CO—O—, Ar—$R^3$—CO—S—, Ar—$R^3$O—, Ar—$R^3$S—, in which $R^3$ and $R^{3'}$ are as defined above, and Ar denotes an aryl groups, especially a phenyl group; aromatic and non-aromatic heterocyclic groups, for example, having one or more heteroatoms, for example, up to 3 heteroatoms, which may be the same or different, selected from nitrogen, oxygen and sulphur atoms, and preferably up to 14 atoms in total, and the corresponding heterocyclicoxy groups and heterocyclicthio groups. When R represents other than an aliphatic group, a further possible substituent is a lower alkyl group.

The group R may be removable by hydrolysis, by photolysis, by reduction or by enzyme action to give the free acid, or two or more methods may be used, for example, reduction followed by hydrolysis. A group R that may be removed readily without substantial degradation of the rest of the molecule is particularly useful as a carboxyl protecting group. Examples of esters that are readily split by reduction are arylmethyl esters, for example, benzyl, p-nitrobenzyl, benzhydryl and trityl esters. Reduction of an ester, for example, an arylmethyl ester, may be carried out using hydrogen and a metal catalyst, for example, a noble metal, for example, platinum, palladium or rhodium, which catalyst may be supported, for example on charcoal or kieselguhr.

Alternatively, a p-nitrobenzyl ester may be converted to the free acid by a two-step method, with an initial reduction of the nitro group, followed by hydrolysis. The nitro group may be reduced by noble metal catalysed hydrogenation, for example, using platinum, or palladium on carbon, or by a metal reducing agent, for example, zinc in acetic acid. Other metal reducing agents are, for example, aluminium amalgam, and iron and ammonium chloride, see, for example, British Patent Specification No. 1,582,960. Reduction of the nitro group is followed by hydrolysis which may occur in situ during reduction of the nitro group or which may be carried out subsequently by treatment with an acid or a base. An o-nitrobenzyl ester may be converted to the free acid by photolysis.

A stannyl ester, for example, a tri-n-butyl stannyl ester, may be split readily by hydrolysis, for example, by solvolysis, for example, using water, an alcohol, a phenol or a carboxylic acid, for example, acetic acid.

Certain ester groups may be split off by base hydrolysis, for example, acetylmethyl and acetoxymethyl ester groups.

There may be used an esterifying group that is removable under physiological conditions, that is to say, the esterifying group is split off in vivo to give the free acid or the carboxylate, for example, an acyloxymethyl ester, e.g. an acetoxymethyl or pivaloyloxymethyl ester, an aminoalkanoyloxymethyl ester, for example, an L-gylclyoxymethyl, L-valyloxymethyl or L-leucyloxymethyl ester, or a phthalidyl ester, or an optionally substituted 2-aminoethyl ester, for example, a 2-diethylaminoethyl or 2-(1-morpholino)-ethyl ester.

Preferred esters are the p-nitrobenzyl, phthalidyl, pivaloyloxymethyl, acetylmethyl and acetoxymethyl esters.

An ester of formula I, or of any other free acid described herein, may be prepared by reaction with an alcohol, phenol or stannanol, or a reactive derivative thereof. The reaction is preferably carried out under mild conditions in order to prevent rupture of the ring or ring system, for example, under neutral or mild acidic or basic conditions, and at temperatures within the range of from −70° to +35° C.

An alkyl, alkoxyalkyl or aralkyl ester may be prepared by reaction of an acid of formula I or any other free acid with the appropriate diazoalkane or diazoaralkane for example, diazomethane or diphenyldiazomethane. The reaction is preferably carried out in an ether, ester or halogenhydrocarbon as solvent, for example, in diethyl ether, ethyl acetate or dichloromethane. In general, temperatures below room temperature are preferred, for example, from −15° to +15° C.

An ester derived from an alcohol may also be produced by reaction of a reactive derivative of the alcohol, for example, a halide, for example a chloride, bromide or iodide, or a hydrocarbonsulphonyl derivative, for example, a mesyl or tosyl ester, with a salt of an acid of formula I or another free acid described herein for example, an alkali or alkaline earth metal salt, for example, a lithium, sodium, potassium, calcium or barium salt or an amine salt, for example, a triethylammonium salt. This reaction is preferably carried out in a substituted sulphoxide or amide solvent for example, in dimethyl sulphoxide, dimethylformamide or hexamethylphosphoramide or, alternatively, an ester may be prepared by reaction of the acid with the alcohol in the presence of a condensing agent, for example, dicyclohexylcarbodiimide.

A stannyl ester may be formed by reaction of a carboxylic acid of formula I or another free acid described herein, or a salt thereof with a reactive tetravalent tin compound, especially a trialkyl tin oxide.

The present invention also provides the salts of those compounds of formula I that have salt-forming groups, especially the salts of free acids of formula I and the acid addition salts of compounds of formula I having a basic group. The salts are especially physiologically tolerable salts, for example, alkali metal and alkaline earth metal salts, for example, sodium, potassium, lithium, calcium and magnesium salts, ammonium salts and salts with an organic amine; also physiologically tolerable acid addition salts. These may be formed, with suitable inorganic and organic acids, for example, hydrochloric acid, sulphuric acid, organic carboxylic and organic sulphonic acids, for example, trifluoroacetic acid and p-toluene-sulphonic acid. Some compounds of formula I which contain a basic centre may exist as Zwitterions; such salts are also part of this invention.

A salt of a free acid of formula I may be produced by reacting the free acid with the appropriate base in a solvent, preferably under conditions under which the salt precipitates. A preferred base is potassium ethyl hexanoate.

A salt may be produced directly from an ester by splitting off the ester group under suitable reaction conditions, for example, catalytic reduction of an ester, for example, a p-nitrobenzyl ester, in an aqueous/organic solvent, for example, comprising water and ethyl acetate, dioxane, or tetrahydrofuran, in the presence of a metal salt, especially a bicarbonate, for example, in an equivalent amount or in a slight excess, yields a salt directly.

Compounds of the general formula I may be produced, for example, as shown in the reaction scheme below.

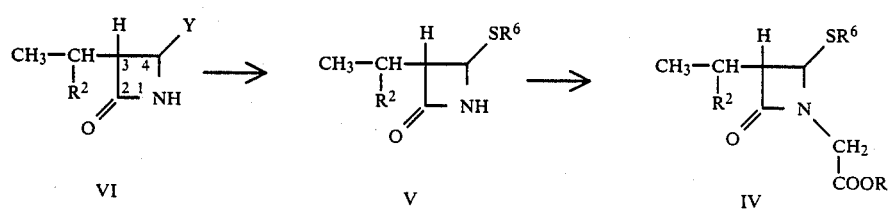

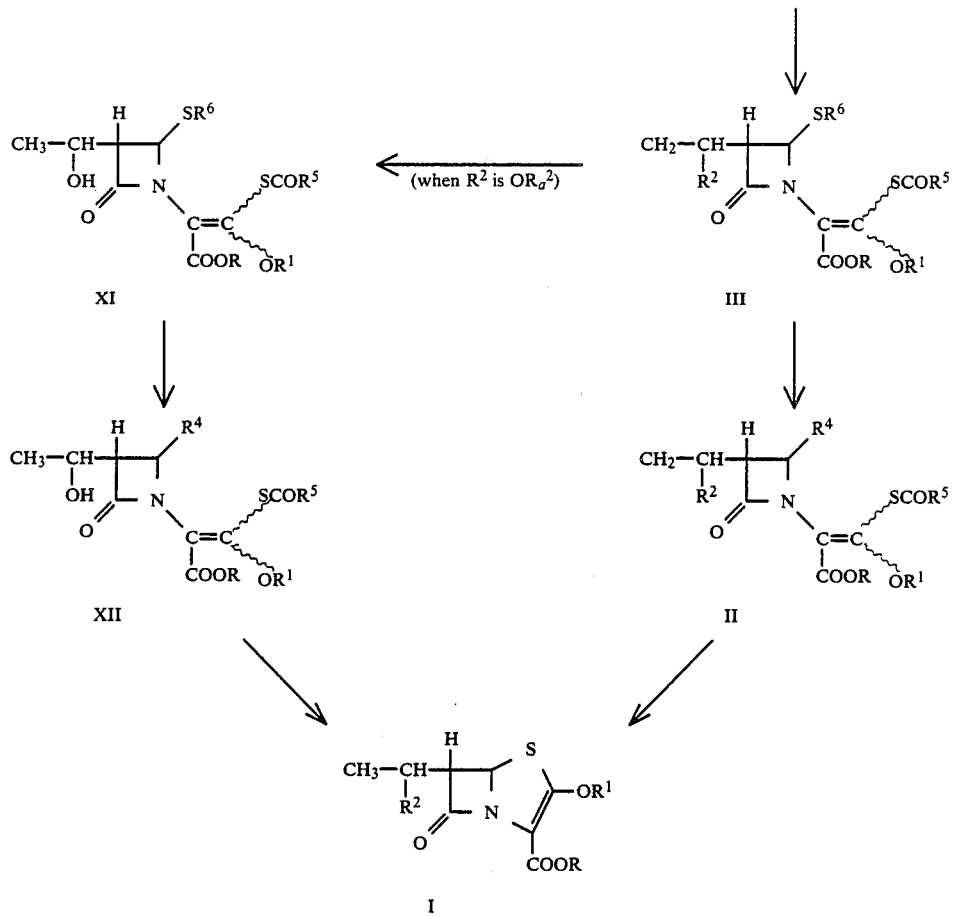

in which R, $R^1$, $R^2$, $R^4$ and $R^5$ are as defined above, $R_a^2$ represents a hydroxyl protecting group, $R^6$ is defined below, and Y represents a group that is capable of being replaced by a nucleophilic group and is especially an acyloxy group, a sulphonyl group, or a halogen atom. An acyloxy group is especially a lower alkylcarbonyloxy group, in particular an acetoxy group. A halogen atom is especially a chlorine atom. A sulphonyl group is a group —$SO_2R^7$ in which $R^7$ represents an alkyl group having from 1 to 4 carbon atoms, or an aryl group, especially a phenyl group.

A compound of formula VI in which $R^2$ represents a hydrogen atom may be prepared as described in Liebigs Annalen Chemie 1974, pp 539–560, Claus, Grimm and Prossel, DT-OS 1 906 401, UK Specification No. 2 013 674, Chem. Pharm. Pharm. Bull, 29 (7) 1854, or H. R. Pfaendler, J. Gosteli and R. B. Woodward, J.A.C.S. 102: 6, 1980, 2039–2043, and certain compounds in which $R^2$ represents a modified hydroxyl group may be prepared as described in Belgian Patent Specification No. 882 764 ($R^2$ represents a dimethyl-t-butylsilyloxy group), and E.P.A. 2210 ($R^2$ represents a p-nitrobenzyloxycarbonyloxy group).

A compound of formula VI may be converted into a compound of formula V by reaction with a compound of formula VII $R^8$—S—$R^6$  VII in which $R^6$ represents an alkyl group having from 1 to 8, preferably from 1 to 4 carbon atoms, an alkenyl group having 3–8 carbon atoms, or a phenyl group, and $R^8$ represents a hydrogen atom or an alkali metal atom, especially a sodium or potassium atom. $R^6$ preferably represents an allyl group or a straight chain, lower alkyl group, especially an ethyl group.

The reaction is generally carried out in a solvent, preferably a protic solvent, for example, water or an alcohol, or a non-protic, water-miscible solvent which is preferably polar, for example, dimethylformamide, dimethyl sulphoxide, tetrahydrofuran or dioxan. The reaction temperature is, for example, from $-20°$ to $+50°$ C., preferably from $-10°$ to $+20°$ C.

To obtain a compound of formula IV, a compound of formula V may be reacted, in the presence of a base, with a compound of formula VIII $Y^1CH_2CO_2R$  VIII in which R is as defined above and $Y^1$ represents a group that is capable of being replaced by a nucleophilic group and is, for example, a halogen atom, preferably a bromine or iodine atom, or a modified hydroxy group, preferably a sulphonyloxy group of the formula

—$OSO_2R^9$ in which $R^9$ represents a lower alkyl or —$CF_3$ group, or a phenyl group which is unsubstituted or is substituted by a p-nitro, p-bromo or p-methyl group.

$Y^1$ preferably represents a bromine or iodine atom or a methylsulphonate, trifluoromethylsulphonate, tolylsulphonate or benzenesulphonate group.

The base may be inorganic, organic or organometallic, for example, an alkali metal or alkaline earth metal hydroxide, oxide, carbonate, bicarbonate or hydride, for example, sodium hydroxide, magnesium oxide, potassium carbonate, potassium bicarbonate or sodium hydride; a tertiary amine, for example, a trialkylamine, for example, triethylamine, DABCO (diazabicyclo[2,2,-2]octane), pyridine, or an alkyl-substituted or amino-substituted or dialkylamino-substituted pyridine, for example, N,N-dimethylaminopyridine, or collidine; a guanidine, for example, tetramethylguanidine, DBN (diazabicyclo[4,3,0]non-5-ene), or DBU (diazabicyclo[5,4,0]undec-7-ene); a polymeric base, i.e. a base attached to an inert polymeric support e.g. Hünig's base (diisopropylethylamine attached to e.g. polystyrene); a metallated amine, for example, a metallated alkyl or arylamine, for example, lithium diisopropylamide (LDA), lithium hexamethyldisilazide, lithium piperidide, lithium 2,2,6,6-tetramethylpiperidide, or a Grignard reagent, for example, methylmagnesium bromide. Preferred bases are, for example, potassium carbonate, sodium hydride, lithium diisopropylamide and triethylamine.

The reaction is generally carried out in an aprotic solvent or diluent, for example, a tertiary amide, for example, dimethylformamide, dimethylacetamide or hexamethylphosphoramide; a hydrocarbon, for example, benzene or toluene; or an ether, for example, diethyl ether, tetrahydrofuran or dioxane; a chlorinated hydrocarbon, for example, methylene chloride or chloroform; or acetonitrile, dimethyl sulphoxide, or sulpholane. Dimethylformamide and dimethylacetamide are preferred. A mixture of two or more solvents and/or diluents may be used.

The reaction may be carried out at a temperature generally within the range of from $-80°$ C. to $+30°$ C. preferably from $-40°$ to $+30°$ C., and especially from $-20°$ to $+20°$ C.

From 1 to 1.5 moles of compound VIII are preferably used per mole of compound V, especially from 1 to 1.1 moles of VIII per mole of V. The base is used in an amount for example, from 1 to 4 moles of base per mole of compound V.

The reaction is preferably carried out by dissolving compound V in a solvent, advantageously in dimethylformamide, with stirring, adding the base, adding the compound of formula VIII and reacting at the desired temperature. The resulting compound of formula IV may be worked up and isolated in the usual manner, for example, using chromatographic and/or crystallisation techniques, or the subsequent reaction may be carried out directly on the resulting reaction mixture after removal of any solvent that is not compatible with the subsequent reaction.

If R in formula IV represents a carboxyl esterifying group, this group may be converted into another esterifying group R, for example, to introduce a group R that is more easily removable under desired conditions. This transesterification is generally carried out as follows: the ester of formula IV is hydrolysed in known manner using, for example, acid or alkaline hydrolysis, preferably using an alkali metal hydroxide, especially sodium or potassium hydroxide. The ester of formula IV, for example, a methyl ester, is preferably hydrolysed using an alkali metal hydroxide especially one mole thereof per mole of the ester of formula IV in a solvent, for example ethanol, methanol or water, or an aqueous-organic solvent, for example, tetrahydrofuran/water, ethanol/water, or acetonitrile/water.

The reaction mixture may then be acidified to give a solution of pH 1 to 5, preferably 2 to 4, and the free acid may then be isolated and, if desired, the free acid is then esterified with an esterifying agent capable of introducing a different esterifying group R, for example with an alcohol ROH in the presence of an acid or another activating agent, for example, dicyclohexylcarbodiimide, or with an alkylating agent $RY^1$ in which $Y^1$ is as defined above. Alternatively, a salt may be isolated and esterified directly. Esterification methods are described above in relation to the compound of formula I.

Transesterification may be carried out on compound IV as described above, or on any other intermediate or on the final product of formula I.

A compound of formula IV may be converted into a compound of formula III by reaction, in the presence of a base, with a compound of formula IX

in which $R^1$ is as defined above, followed by reaction with an activated carboxylic acid derivative which comprises the group $R^5$, for example, a compound of formula X

in which $R^5$ is as defined above.

Some compounds of formula IX are known and some are new. New compounds may be prepared by processes analogous to those for the preparation of the known compounds. cf. River & Schalch, Helv. Chem. Acta, Vol 6, 1923, p. 605, and Reich & Martin, Chem Berichte, Vol 98, 1965 p. 2063.

The reaction between compound IX and compound IV is carried out in the presence of a base, preferably having a $pK_a \geq 20$, preferably a metallated amine, and examples of preferred bases are lithium diisopropylamide, lithium hexamethyldisilazide, lithium 6,6,2,2-tetramethylpiperidide, lithium cyclohexyl isopropylamide, and sodamide.

The reaction is generally carried out in an aprotic solvent, for example, an oxygenated hydrocarbon, preferably an ether, for example, diethyl ether, tetrahydrofuran, dioxane, glyme or diglyme. The reaction temperature is, for example, from $-120°$ to $+30°$ C., preferably from $-78°$ to $-20°$ C.

The amount of base used is, for example, from 1 to 3 moles, calculated per mole of compound IV, preferably from 1.5 to 2.5 moles of base. The compound of formula IX is preferably used in an amount of from 1 to 1.5 moles per mole of compound IV, preferably from 1 to 1.1 moles of compound IX.

The reaction is preferably carried out as follows: to a stirred solution of compound IV under an inert atmosphere is added the base and subsequently a solution of compound IX in the same or a different solvent.

The activated acid derivative, preferably of formula X, is preferably added to the mixture resulting from the reaction of compounds IV and IX especially in an amount of from 1 to 2 moles calculated on compound IV. The reaction is preferably carried out at a temperature of from −80° to +40° C., adding the compound of formula X to the reaction mixture at the temperature at which the reaction between compounds IV and IX took place, and then warming, or allowing the mixture to warm, to room temperature, if desired, heating the mixture to a temperature of up to 40° C.

The —SCOR$^5$ group in the resulting compound of formula III may be cis or trans to the —COOR group. The isomers may be separated for the subsequent reaction, but this is not generally necessary, and the isomeric mixture is generally used.

It is preferable to protect a free hydroxy group $R^2$ before the formation of compound III, to prevent the free hydroxy group from reacting with the compound of formula IX and/or with the activated carboxylic acid derivative. The protective group may be introduced into compound IV before its conversion into compound III, or it may be introduced at an earlier stage in the reaction sequence eg. in compound V or VI.

A compound of formula II may be produced from a compound of formula III directly by halogenation.

The halogenation is carried out with an agent capable of splitting a carbon-sulphur bond and introducing a halogen atom. Such agents are well known in the art and include, for example, molecular chlorine, molecular bromine, sulphuryl chloride, sulphuryl bromide, t-butylhypochlorite and cyanogen chloride.

The reaction is generally carried out at a temperature within the range of from −40° to +20° C. The reaction is generally carried out in a solvent or diluent that is non-protic and is inert under the reaction conditions, for example, an ether, a hydrocarbon or a halogenated hydrocarbon, for example, dioxane, benzene, chloroform or methylene chloride. A mixture of two or more solvents may be used. Examples of halogenating systems are: chlorine in chloroform and, especially, chlorine in benzene and t-butylhypochlorite in benzene. In the latter two cases, the temperature is preferably from 5° to 20° C., and especially from 5° to 10° C. Generally 1 to 2 moles of chlorine, bromine or cyanogen bromide are used per mole of compound III. (cf. S. Kukolja J. Amer. Chem. Soc. (1971) 93 6267, and P. C. Cherry, C. E. Newall and N. S. Watson, J.C.S. Chem. Comm. 1979 p. 663.)

Before halogenation, however, it is preferable to remove the protective group $R_a^2$ from a hydroxy group $R^2$ in compound III, in order to obtain the more desired 5R stereochemistry in the final product. The protective group may be removed in any conventional manner (see below) to give compound XI. Preferred hydroxy-protecting groups $R_a^2$ are those which are compatible with the synthesis of the compound of formula III and which may be removed under reaction conditions in which the resulting compound XI is stable. Compound XI has been found to be stable in the presence of a proton source, for example, hydrogen chloride, aqueous hydrochloric acid or aqueous hydrofluoric acid. Accordingly, one type of preferred hydrory protecting groups $R_a^2$ are those which may be removed under acidic conditions. Such groups are well known in the art and are, for example, tetrahydropyranyl and tetrahydrofuranyl groups; acetal and ketal groups, for example, of formula

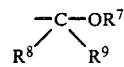

in which $R^8$ and $R^9$, which may be the same or different, each represents a hydrogen atom or a lower alkyl group, preferably a methyl group, or $R^8$ and $R^9$ together with the carbon atom to which they are attached, represent a cycloalkyl ring having from 4 to 7 carbon atoms, or a tetrahydropyranyl ring, and $R^7$ represents a lower alkyl group, preferably a methyl or ethyl group; also silyl esters, for example, as described above in relation to R, for example, —SiR$^{10}$R$^{11}$R$^{12}$ groups, in which $R^{10}$, $R^{11}$ and $R^{12}$, which may be the same or different, each represents a lower alkyl group or an aryl group, for example, triethylsilyl, t-butyldimethylsilyl and methyldiphenylsilyl groups; and stannyl groups, for example, as described above in relation to R, for example, —SnR$^{13}$R$^{14}$R$^{15}$ groups, in which $R^{13}$, $R^{14}$ and $R^{15}$, which may be the same or different, each represents a lower alkyl group, for example, a tri-n-butylstannyl group. Preferred $R_a^2$ groups are tetrahydropyranyl, 2-methoxypro-2-yl, trimethylsilyl, triethylsilyl and, especially, t-butyldimethylsilyl groups.

Such groups may be removed by acid hydrolysis, for example, using moderately concentrated hydrochloric acid, eg. 6M HCl, eg. in tetrahydrofuran (cf. Belgian Patent Specification No. 881 012); t-Bu$_4$NF in an acidic medium eg. in acetic acid (cf. Belgian Patent Specification No. 882 764): or aqueous hydrogen fluoride, eg. in the presence of acetonitrile (cf. J. Chem. Soc. Perkin 1, 1981, 2055).

The halogenation of compound XI to give compound XII may be carried out substantially as described above. The halogenating agent is generally used in an amount of from 1 to 2 mole equivalents, calculated on the compound of formula XI.

It has been found, surprisingly, that halogenation of a compound of formula XI that has 4R stereochemistry gives predominantly the corresponding 4S compound of formula XII, whereas halogenation of the corresponding 4R compound of formula III having a protected hydroxy group $R^2$ gives predominantly the less desired 4R halogenated-compound.

A compound of formula I is produced from a compound of formula II or XII by reaction with a base. The base must be capable of splitting the thiocarbonyl bond in a compound of formula II or formula XII and of bringing about ring closure. The base may be inorganic or organic, for example, ammonia, or an alkali metal, especially a sodium or potassium, carbonate, bicarbonate, or hydroxide; a primary amine, for example, methylamine, ethylamine, aniline or benzylamine; an alkali metal alkoxide in the corresponding alcohol, for example, sodium methoxide in methanol; or a heterocyclic base, for example, having a pK$_a$ within the range of from 5 to 9, for example, imidazole or pyridine or a substituted pyridine, for example, an alkyl, amino, or alkylamino-substituted pyridine, for example, 4-methyl-, or 4-dimethylaminopyridine. Imidazole is particularly preferred.

The reaction is generally carried out in a solvent or diluent, the choice of which is wide, provided that it is inert under the reaction conditions. Examples of solvents and diluents are oxygenated hydrocarbons, for example, alcohols, for example, having up to 4 carbon atoms, for example, methanol and ethanol; ethers, for example having up to 4 carbon atoms, for example, diethyl ether, also tetrahydrofuran and dioxane; ketones, for example, having up to 4 carbon atoms, for example, acetone and methyl ethyl ketone; esters, for example, methyl acetate and ethyl acetate; and amides, for example, dimethylformamide and dimethylacetamide; also chlorinated hydrocarbons, for example, chloroform, methylene chloride and carbon tetrachloride; aromatic hydrocarbons, for example, benzene and toluene; and other solvents for example, acetonitrile and nitromethane. A mixture of any two or more solvents may be used, and solvents are preferably used in admixture with water, preferably a water-miscible solvent in admixture with 5 to 20% (v/v) water.

The reaction is generally carried out at a temperature within the range of from 0° to 40° C., preferably from 0° to 20° C.

It is preferable to esterify any free carboxyl group present in a compound of formula II or formula XII prior to conversion to a compound of formula I. Although an ester group may be introduced immediately prior to this conversion, it is preferable to esterify the carboxyl group at an earlier stage in the preferred reaction sequence, for example, to esterify a free carboxyl group in a compound of formula III, IV or XII to ensure that the carboxyl group does not take part in any of the subsequent reactions. An esterifying group may be transesterified to another ester group having more desirable properties for a particular stage of the reaction sequence.

Furthermore, it is advisable to protect any reactive moiety present in either R or $R^1$ so that such a moiety does not react with any of the reagents used in any subsequent reaction. Examples of moieties which may require protection are hydroxy, carboxy and amine moieties which may, for example react with the reagents used to convert a compound IV to a compound III. Groups suitable for protecting such reactive moieties are well known, as are methods for their removal. (cf. Protective Groups in Organic Chemistry, editor J. F. W. McOmie, Plenum Press, 1973). (The special considerations with regard to a free hydroxy group $R^2$ are given above.)

Hydroxy-protecting groups are exemplified above.

Carboxy-protecting groups are, for example, as described above for R. Amino protecting groups are, for example, t-butyloxycarbonyl, benzyloxycarbonyl, p-nitrobenzyloxycarbonyl, p-nitrobenzenesulphenyl and trityl groups.

Reactive moieties may be protected at any appropriate point in the reaction sequence, and the protective groups are preferably removed after the formation of the compound of formula I, for example, if R in formula I represents an esterifying group, this may be removed in the usual manner, depending on the nature of the ester group, for example, by hydrolysis, reduction, or enzymatically, to yield the free acid. A free acid or an ester may be converted into a salt, especially a physiologically tolerable salt, or a salt may be converted into another salt or the free acid or an ester. An ester may be transesterified, or a free acid converted into an ester, for example, to give an ester capable of removal under physiological conditions. Examples of such procedures are given above.

If $R^2$ in a compound of formula I represents a protected hydroxy group, the protecting group may be removed. Conversely, if $R^2$ represents a free hydroxy group, this may be converted into a protected hydroxy group, especially one in which the protecting group is physiologically removable, for example, a group of the formula $$R^{10}CO- \text{ or } R^{11}-$$

in which $R^{10}$ represents a hydrogen atom or a straight or branched chain alkyl group having from 1 to 4 carbon atoms, especially a methyl, ethyl or t-butyl group, or represents a phenyl group or a phenoxyalkyl group in which the alkyl moiety is straight-chained or branched and has up to 4 carbon atoms, and is especially a methyl group; and $R^{11}$ represents an alkanoyloxymethyl group in which the alkane moiety is a straight or branched chain alkyl group having up to 4 carbon atoms, and is especially a methyl or t-butyl group. Preferred physiologically removable protecting groups for a hydroxy group $R^2$ are acetyl, propionyl, pivaloyl, benzoyl, phenoxymethylcarbonyl, pivaloyloxymethyl and acetoxymethyl groups. In a compound of formula I, a hydroxy protecting group that is not removable under physiological conditions may be converted into one that is removable under such conditions. An advantage of physiologically removable protecting groups is that they appear to increase the oral absorbability of the compounds of formula I.

The invention also provides a modification of the process described above, wherein in a compound of formula I, II, III, XI or XII or in more than one of these compounds, a substituent of a group $R^1$ is converted at an appropriate point in the reaction sequence into another substituent of $R^1$. A substituent of $R^1$ in compound III, for example, may be converted into another substituent of $R^1$ before the halogenation reaction to give compound II, or the initial substituent of $R^1$ may be retained during the halogenation reaction, being converted into another substituent of $R^1$ before the reaction of compound II to give compound I.

The following are examples of interconversions of substituents of $R^1$:

---

$R^3S-$ to $R^3SO-$
$R^3S-$ or $R^3SO-$ to $R^3SO_2-$
$NO_2-$ to $NH_2-$, which may then be alkylated or acylated,
$CN-$ to $CH_2NH_2-$, which may then be alkylated or acylated,
$N_3$ to $NH_2-$, which may then be alkylated or acylated,
$HO-$ may be alkylated or acylated
$R^3CO-O-$ to $HO-$, which may then be alkylated or acylated,
Halogen to $-SH, -SO_2H, -SO_3H$ or $-CN$

---

The methods for carrying out such reactions are known in the art, for example, an alkylthio group may be oxidised, preferably with a carboxylic peracid, especially m-chloroperbenzoic acid, to give the corresponding alkylsulphinyl or alkylsulphonyl group; a nitro group may be reduced to an amino group by noble metal catalysed hydrogenation, for example, using platinum, or 10% palladium on carbon, c.f. M. Freifelder, Catalytic Hydrogenation in Organic Synthesis, Willey Interscience, 1978, page 26, and P. N. Rylander, Catalytic Hydrogenation over Platinum Metals, Academic Press, 1967, Chapter 11; an amino group may be alkylated with a conventional alkylating agent, for example, a lower alkyl halide, for example, methyl iodide, or acylated with, for example, an acid chloride or acid anhydride, for example, acetyl chloride or acetic anhydride, a cyano group may be converted into an amino group by reduction, for example, using a metal hydride; an azide group may be converted into an amino group by reduction, for example, using hydrogen sulphide or catalytic reduction; and a hydroxy group may be alkylated or acylated as described above and a halide, especially an iodide, may be treated with an organometallic compound, for example an organolithium compound, especially t-butyllithium, the resulting complex being treated with sulfur, sulfur dioxide or cyanogen to give the —SH, —SO$_2$H or —CN group respectively.

These modifications of the process of the invention are particularly useful for the production of a compound of formula I having a group R$^1$ bearing 1, 2 or 3 substituents, any one or more of which is potentially unstable or incompatible during any one or more of the stages of the reaction sequence described above. The conversion step is, accordingly, carried out after the step in which the substituent is potentially unstable or incompatible.

It will be appreciated that although these modifications are particularly useful for the production of compounds of formula I having substituents on R$^1$ that are potentially unstable in the production process, it is not limited to such groups, and in a further modification of the process of the invention, a substituent of R$^1$ may be produced by conversion of another substituent that does not itself fall within the definition of a substituent of R$^1$, for example, an unsubstituted or substituted, preferably p-nitrosubstituted, benzyloxycarbonylamino group may be converted into a free amino group, for example, by noble metal catalysed hydrogenation, c.f. M. Freifelder, loc. sit., page 111, P. N. Rylander, loc. cit., page 455, and c. Berse et al, J. Org. Chem. 22, 805, 1957.

At each stage of the preferred reaction sequence, the desired compound may be isolated from the reaction mixture and, if desired, purified by appropriate techniques generally used for the purification of organic compounds, for example, chromatography or crystallisation.

As indicated above, various intermediates may be produced in the form of mixture of isomers of various kinds. Such a mixture may be separated or resolved at any stage, or the isomeric mixture may be used per se for subsequent reactions. (In the case where a protective group R$^2$ has been removed before halogenation, a resulting compound of formula XII is preferably separated into the 4R and 4S isomers (see below)).

All of the compounds that are provided by the invention may exist in any isomeric form, as discussed above, either as a pure isomer or as a mixture of any two or more isomers.

A compound of formula I may have the R- S-stereochemistry independently at positions 5 and 6, and also at position 8 when R$^2$ represents a hydroxy or protected hydroxy group. Further isomeric forms will occur when any substituent contains a chiral carbon atom. Any mixture of two or more isomeric forms may be resolved if desired, or a compound of formula I can be used in the form of the isomeric mixture. The preferred stereochemistry at position 5 in compound I is generally R, corresponding to that in naturally occurring penicillins and cephalosporins, at position 6 is S, and at position 8 is R.

If a 3S-compound of formula III in which R$^2$ represents a protected hydroxy group is converted into a compound XI before halogenation, ie. if the protecting group is removed before halogenation, it has been found that the resulting compound of formula I is predominantly the desired 5R, 6S isomer. The following reaction scheme illustrates the stereochemistry, R, R$^1$, R$_a^2$, R$^4$ and R$^5$ being defined as above.

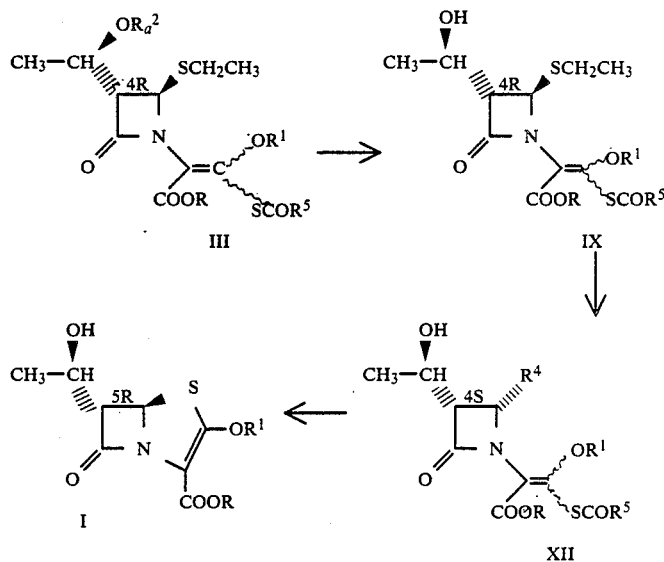

Halogenation of the 4R compound of formula XI gives predominantly the 4S compound of formula XII. The proportion 4S:4R compound XII depends on the halogenating agent used and the reaction conditions, but in general varies from 3:1 to amounts as high as 9:1. The 4R and 4S isomers can be separated readily, for example, by chromatography. A compound of formula XI also has E/Z isomerism at the double bond, so the 4R and 4S isomers may be further separated into the individual E and Z isomers. This is not generally necessary, but the 4R and 4S isomers are preferably separated before conversion into a compound of formula I. As can be seen from the reaction scheme, a 4S compound XII is converted by reaction with a base into a 5R compound I. If, however, a 3S-compound of formula III having a protected hydroxy group R² is halogenated directly, the resulting compound II is 4R, and the resulting compound I is 5S. As the preferred stereochemistry at position 5 is R, it will be appreciated that it is preferable to deprotect before halogenation.

The compounds of formula I and salts thereof are β-lactamase inhibitors, and the compounds are generally stable to the action of β-lactamases produced by grampositive organisms, for example, by *Staphylococcus aureus* and gram negative organisms, for example, *Enterobactercloacae*. They also possess antibacterial properties themselves and may be used in humans and other animals, for example, to treat bacterial infections caused by gram-positive and gram-negative bacteria, for example, *Staphylococcus aureus, Streptococcus pyrogenes, Bacillus subtilis, E. coli, Pseudomonas aeruginosa,* and *Proteus morganii,* some strains of which are penicillin-resistant.

The invention accordingly provided a pharmaceutical preparation which comprises a compound of formula I, or a physiolgically tolerable salt thereof, or a mixture of two or more such substances as active ingredient, in admixture or conjuction with a pharmaceutically suitable carrier. The preparation may also comprise one or more other pharmaceutically active substances, for example, another antibacterial substance, especially one which has a β-lactam ring. The preparations may be in a form suitable for enteral or parenteral administration, for example, for oral, intravenous, or intramuscular administration, for example, as tablets, capsules, syrups, or sterile injectable or infusible solutions. The preparations are advantageously in unit dosage form and preferably comprise from 10 to 2000 mg of the active ingredient. The daily dosage of the active ingredient is generally from 20 to 8000 mg, in divided doses, generally up to 4 doses.

The invention also provides the use of an active ingredient as defined above as a β-lactamase inhibitor and/or as an antibacterial agent.

The invention further provides a pharmaceutical preparation which comprises an active ingredient as defined above, in unit dosage form.

The invention also provides a pharmaceutical preparation which comprises an active ingredient as defined above, or a physiologically tolerable salt thereof or a mixture of two or more such substances, and one or more further pharmaceutically active substances, for example, as described above and, for example, in unit dosage form.

Unit dosages are preferably as described above.

The following Table provides examples of compounds of the invention.

TABLE

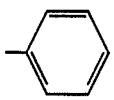

| R | R¹ | R² |
|---|----|----|
| H | phenyl | H |
| H | phenyl | OH |
| H | 4-Cl-phenyl | H |
| H | 4-Cl-phenyl | OH |
| H | 4-F-phenyl | H |
| H | 4-F-phenyl | OH |
| H | 4-CH₃-phenyl | H |
| H | 4-CH₃-phenyl | OH |
| H | 4-OCH₃-phenyl | H |
| H | 4-OCH₃-phenyl | OH |
| H | 4-CF₃-phenyl | H |
| H | 4-CF₃-phenyl | OH |
| H | 4-NO₂-phenyl | H |

TABLE-continued

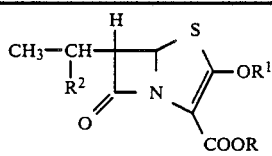

| R | R¹ | R² |
|---|---|---|
| H | 4-NO₂-C₆H₄- | OH |
| H | 2,4,5-(OCH₃)₃-C₆H₂- | H |
| H | 2,4,5-(OCH₃)₃-C₆H₂- | OH |
| H | 2,5-dimethyl-thien-3-yl | H |
| H | 2,5-dimethyl-thien-3-yl | OH |
| H | pyridin-3-yl | H |
| H | pyridin-3-yl | OH |
| H | 2,6-dimethyl-pyridin-3-yl | H |
| H | 2,6-dimethyl-pyridin-3-yl | OH |
| H | 4-NHCOCH₃-C₆H₄- | H |
| H | 4-NHCOCH₃-C₆H₄- | OH |

TABLE-continued

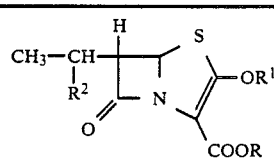

| R | R¹ | R² |
|---|---|---|
| H | 4-NH₂-C₆H₄- | H |
| H | 4-NH₂-C₆H₄- | OH |
| H | thien-3-yl | H |
| H | thien-3-yl | OH |
| H | 4-SCH₃-C₆H₄- | H |
| H | 4-SCH₃-C₆H₄- | OH |
| H | 4-S(O)CH₃-C₆H₄- | H |
| H | 4-S(O)CH₃-C₆H₄- | OH |
| H | 4-CN-C₆H₄- | H |
| H | 4-CN-C₆H₄- | OH |
| H | 4-COOCH₃-C₆H₄- | H |

TABLE-continued structure: CH3-CH(R2)-C(=O)-N ring with S, bearing H, OR1, and COOR, forming a bicyclic β-lactam

| R | R¹ | R² |
|---|---|---|
| H | phenyl-C(=O)-OCH₃ | OH |
| H | phenyl-NH-SO₂-CH₃ | H |
| H | phenyl-NH-SO₂-CH₃ | OH |
| H | phenyl-NH-CO-NH-CH₃ | H |
| H | phenyl-NH-CO-NH-CH₃ | OH |
| H | phenyl-SO₂-CH₃ | H |

Alternatively, for each of the above compounds P may represent Na⁺, K⁺, Li⁺ or a pivaloyloxymethyl or phthalidyl group.

The stereochemistry at position 5 is preferably P. When R² represents a free or protected hydroxyl group, the stereochemistry at position 6 is preferably S, and at position 8 is preferably R.

Furthermore, in each of the above compounds (salts and esters), in which R² represents a hydroxy group, this group may be protected by an acetyl, propionyl, pivaloyl, benzoyl, phenoxymethylcarbonyl, pivaloyloxymethyl or acetoxymethyl group.

The present invention also provides compounds of the general formulae II, III, IV, V, XI & XII, and more especially provides the compounds specifically described in the Table, and in the Examples given hereinafter.

The following Examples illustrate the invention. In them, temperatures are expressed in degrees Celsius, and T.L.C. denotes thin layer chromatography.

EXAMPLE 1

4-Allylthio-3-ethylazetidin-2-one

To a stirred solution of 3.2 g of sodium hydroxide in 40 ml of water under an argon atmosphere were added 8 ml of allyl thiol (about 85% pure). After 20 minutes of further stirring, a solution of 12.5 g of 4-acetoxy-3-ethylazetidin-2-one in 20 ml of water was added and the mixture was stirred for a further 15 minutes, and then extracted into dichloromethane. The organic extracts were washed with water, were dried over MgSO₄, and evaporated in vacuo to dryness. Chromatography over silica gel, eluting with hexane-ethyl acetate mixtures, afforded the title compounds as a yellow oil (3.2 g).

$\nu_{max}$(CDCl₃) 1765 (β-lactam) cm⁻¹; 3420 (NH) cm⁻¹.

δ(CDCl₃) 1.01 (3H, t, J 7Hz, CH₃); 1.73 (2H, m, CH₃CH₂); 2.95–3.35 (3H, m, SCH₂ and 3-H); 4.43 (1H, d, J 2.5 Hz, 4-H); 5.0–5.4 (2H, m, CH₂=C); 5.6–6.3 (1H, m, CH=C); 6.77 (1H, broad, NH).

EXAMPLE 2

Methyl 2-(4-allylthio-3-ethylazetidin-2-on-1-yl)acetate

To a vigorously stirred solution of 2.34 g of 4-allylthio-3-ethylazetidin-2-one in 20 ml of dimethylformamide were added 1.37 ml of methyl bromoacetate and 4.16 g of finely ground potassium carbonate. After 18 hours, the mixture was poured into 75 ml of water, was extracted into ethyl acetate (5×20 ml) and the combined organic extracts were washed with water (6×15 ml), dried over MgSO₄ and evaporated in vacuo to dryness. Chromatography over silica gel, eluting with hexane-ethyl acetate mixtures, afforded the title compound as a yellow oil (3 g).

$\nu_{max}$ (CDCl₃) 1749 (ester) cm⁻¹; 1763 (β-lactam) cm⁻¹.

δ(CDCl₃) 1.05 (3H, t, J 7 Hz, CH₃CH₂); 1.82 (2H, m, CH₃CH₂); 3.22 (3H, m, SCH₂ and 3-H); 3.5–4.43 (5H, s and AB pattern, CH₃O— and CH₂CO—); 4.58 (1H, d, J 2 Hz, 4-H); 4.95–5.35 (2H, m, CH₂=C); 5.5–6.2 (1H, m, CH=C).

EXAMPLE 3

2-(4-Allylthio-3-ethylazetidin-2-on-1-yl)acetic acid

To a stirred solution of 3 g of methyl 2-(4-allylthio-3-ethylazetidin-2-on-1-yl)acetate in 10 ml of absolute ethanol was added dropwise a solution of 0.9 g of potassium hydroxide in a mixture of 12 ml of ethanol and 1 ml of water. After 5 minutes, the mixture was poured into a mixture of 10 ml of dichloromethane and 20 ml of water. After acidification with 13 ml of 2M HCl, the mixture was extracted with further dichloromethane; the dichloromethane extracts were extracted with saturated sodium bicarbonate solution. These aqueous extracts were acidified to pH 1.5 with 5M HCl and then extracted with dichloromethane. These organic extracts were evaporated to dryness to afford the title compound as a white crystalline solid (2.56 g).

δ(CDCl₃) 1.42 (3H, t, J 7 Hz, CH₃); 1.78 (2H, m, CH₃CH₂); 3.30 (3H, m, SCH₂ and 3-H); 3.5–4.55 (2H, AB pattern, NCH₂); 4.60 (1H, d, J 2 Hz, 4-H); 5.0–5.4 (2H, m, CH₂=C); 5.5–6.3 (1H, m, CH=C); 10.41 (1H, s, OH).

EXAMPLE 4

4-Nitrobenzyl 2-(4-allylthio-3-ethylazetidin-2-on-1-yl)acetate

A mixture of 2.5 g of 2-(4-allylthio-3-ethylazetidin-2-on-1-yl)acetid acid, 8 ml of dimethylacetamide and 636 mg of anhydrous sodium carbonate was stirred under argon for 20 minutes, and then 2.59 g of 4-nitrobenzyl bromide were added. After 30 minutes further stirring, the mixture was partitioned between ethyl acetate and water. The organic layer was separated and was washed with saturated sodium bicarbonate, with water, with brine, was dried over MgSO$_4$, and was evaporated in vacuo to dryness. Chromatography over silica gel, eluting with hexane-ethyl acetate mixtures, afforded the title compound as a pale yellow oil. (3.0 g)

$\nu_{max}$ (CDCl$_3$) 1751 (ester) cm$^{-1}$; 1755 (shoulder, β-lactam) cm$^{-1}$.

δ(CDCl$_3$) 1.06 (3H, t, J 7 Hz, CH$_3$); 1.77 (2H, m, CH$_3$CH$_2$); 3.20 (3H, m, SCH$_2$ and 3-H); 3.5–4.50 (2H, AB pattern, NCH$_2$); 4.58 (1H, d, J 2.5 Hz, 4-H); 4.9–5.33 (2H, m, CH$_2$=C); 5.30 (2H, s, OCH$_2$); 5.5–6.3 (1H, m, CH=C); 7.4–8.45

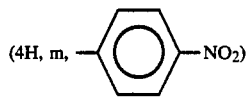
(4H, m, —⟨⟩—NO$_2$)

EXAMPLE 5

4-Nitrobenzyl 2-(4-allylthio-3-ethyl-azetidin-2-on-1-yl)-3-(4-chlorophenoxy)-3-trimethylacetylthiopropenate To a stirred solution of 1 g of 4-nitrobenzyl 2-(4-allylthio-3-ethyl-azetidin-2-on-1-yl)acetate in dry THF at −78° under argon was added a solution of a mixture of 1.3 ml of hexamethyldisilazane and 6.2 mmol of n-butyllithium in dry THF. The mixture was stirred for 30 minutes, and a solution of 0.63 g of p-chlorophenyl chlorothionoformate in 5 ml of dry THF was added. The mixture was warmed at −40° C., and after 30 minutes was then cooled to −78°, and a solution of 0.50 ml of pivaloyl chloride in dry THF was added. The mixture was warmed to room temperature and after 30 minutes, acetic acid was added. The mixture was evaporated to dryness. The resulting oil was partitioned between ethyl acetate and water, the organic layer was separated, washed with water, with aqueous citric acid, with saturated sodium bicarbonate, with brine, and was then dried over MgSO4 and evaporated to dryness. Chromatography over silica gel, eluting with hexane-ethyl acetate mixtures afforded the title compound (1.3 g, 76%) as a yellow oil.

$\nu_{max}$ (CDCl$_3$) 1765 cm$^{-1}$.

δ(CDCl$_3$) 0.85–1.30 (12H, m, (CH$_3$)$_3$, CH$_2$CH$_3$), 1.50–2.20 (2H, m, CH$_2$CH$_3$), 3.00–3.75 (3H, m, SCH$_2$, 3-H), 4.80–5.5 (5H, m, CH$_2$m, CO$_2$CH$_2$, 4H), 6.8–8.3

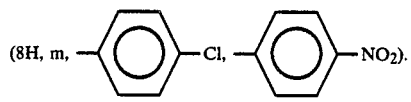
(8H, m, —⟨⟩—Cl, —⟨⟩—NO$_2$).

EXAMPLE 6

4-Nitrobenzyl 2-(4-chloro-3-ethyl-azetidin-2-on-1-yl)-3-(4-chlorophenoxy)-3-trimethylacetylthio-propenate To a solution of 1.3 g of 4-nitrobenzyl 2-(4-allylthio-3-ethyl-acetidin-2-on-1-yl)-3-(4-chlorophenyl)-3-trimethylacetylthiopropenate in dichloromethane at −20°, was added a solution of 4.2 mmol of chlorine in carbon tetrachloride. After 30 minutes the mixture was warmed to room temperature, evaporated in vacuo, and the residual oil was chromatographed over silica gel. Elution with hexane-ethyl acetate mixtures afforded 1.1 g of the title compound as a pale yellow oil (90% of the theoretical yield).

Ratio cis:trans=1:2.5 by NMR $\nu_{max}$ (CDCl$_3$) 1785 cm$^{-1}$.

δ(CDCl$_3$) 0.80–1.30 (12H, m, C(CH$_3$)$_3$, CH$_2$CH$_3$), 1.50–2.15 (2H, m, CH$_2$CH$_3$), 3.00–3.85 (1H, m, 3H), 5.2 (2H, s, CO$_2$CH$_2$), 5.80, 6.05 (1H, 2d, J$_{cis}$ 4 Hz, J$_{trans}$ 1.5 Hz, 4-H), 6.80–8.20

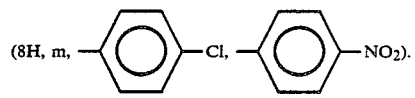
(8H, m, —⟨⟩—Cl, —⟨⟩—NO$_2$).

EXAMPLE 7

4-Nitrobenzyl 3-(4-chlorophenoxy)-6-ethyl-7-oxo-4-thia-1-azabicyclo[3,2,0]hept-2-ene-2-carboxylate To a stirred solution of 1.1 g of 4-nitrobenzyl 2-(4-chloro-3-ethyl-azetidin-2-on-1-yl)-3-(4-chlorophenoxy)-3-trimethylacetylthiopropenate in dioxan-water (9:1 v/v) at 5° C. were added 260 mg of imadazole. After 30 minutes at 5° C. the mixture was warmed to room temperature, and then partitioned between ethyl acetate and water. The organic layer was separated, was washed with water, with aqueous citric acid, with water, with saturated sodium bicarbonate, and with brine, and was then dried over MgSO4, and evaporated in vacuo to dryness. Chromatography over silica gel and elution with ethyl acetate-hexane mixtures afforded 720 mg of the title compound (82%) as a yellow oil.

Ratio cis:trans=2:1 by NMR $\nu_{max}$ (CDCl$_3$) 1795 cm$^{-1}$.

δ(CDCl$_3$) 0.80→1.40 (3H, m, CH$_2$CH$_3$), 1.70–2.4 (2H, m, CH$_2$CH$_3$), 3.50–4.10 (1H, m, 6H), 5.25 (2H, q, CO$_2$CH$_2$), 5.30, 5.65 (1H, 2d, J$_{cis}$ 4 Hz, J$_{trans}$ 1.5 Hz, 5-H), 6.80–8.10

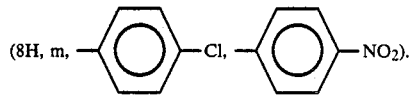
(8H, m, —⟨⟩—Cl, —⟨⟩—NO$_2$).

EXAMPLE 8

Sodium 3-(4-chlorophenoxy)-6-ethyl-7-oxo-4-thia-1-azabicyclo[3,2,0]hept-2-ene-2-carboxylate A mixture of a solution of 205 mg of 4-nitrobenzyl 3-(4-chlorophenoxy)-6-ethyl-7-oxo-4-thia-1-azabicyclo-[3,2,0]hept-2-ene-2-carboxylate in dioxan and 37.5 mg of sodium bicarbonate in water, and 10% palladium/charcoal was hydrogenated at 50 psi at 25° for 60 minutes.

Then, the mixture was filtered through Celite, and then lyophilized to yield 83 mg of the title compound as a pale yellow crystalline solid (53%).

EXAMPLE 9

4-Nitrobenzyl 2-(4-allylthio-3-ethylazetidin-2-on-1-yl)-3-phenoxy-3-trimethylacetylthiopropenate To a stirred solution of 2.0 g of 4-nitrobenzyl 2-(4-allylthio-3-ethylazetidin-2-on-1)-acetate in dry THF at −78° under argon was added a solution of a mixture of 2.07 g of lithium hexamethyldisilazane in dry THF. The mixture was stirred for 5 minutes, and a solution of 1.04 g of phenylchlorothionoformate in 10 ml of dry THF was added. The mixture was warmed to −40°, and after 30 minutes was then cooled to −78°, and a solution of 1.01 ml of trimethylacetyl chloride was added. The mixture was warmed to room temperature and after 15 minutes, the mixture was evaporated in vacuo to dryness. The resulting oil was partitioned between ethyl acetate and water, the organic layer was separated, was washed with water, with aqueous citric acid, with saturated sodium bicarbonate, with brine, was dried over MgSO4 and evaporated to dryness. Chromatography over silica gel, eluting with hexane-ethyl acetate mixtures afforded the title compound (2.58 g, 80%) as a yellow oil.

$\nu_{max}$ (CHCl$_3$) = 1764 cm$^{-1}$.

$\delta$(CDCl$_3$) 0.80–1.30 (12H, m, C(CH$_3$)$_3$, CH$_2$—CH$_3$), 1.55–2.15 (2H, m, CH$_2$—CH$_3$), 3.02–3.43 (3H, m, S-CH$_2$, 3-H), 4.82, 4.95 (1H, 2d, J$_{cis}$ 3 Hz, J$_{trans}$ 1.5 Hz, 4-H), 4.98–5.39 (4H, m, CH$_2$=, CO$_2$CH$_2$), 5.40–6.05 (1H, m, CH=), 6.78–8.28

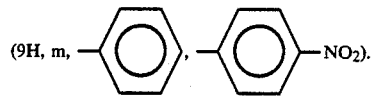

m/e base peak 57.0708, C(CH$_3$)$_3$.

EXAMPLE 10

4-Nitrobenzyl 2-(4-chloro-3-ethyl-azetidin-2-on-1-yl)-3-phenoxy-3-trimethylacetylthiopropenate To a solution of 2.47 g 4-nitrobenzyl 2-(4-allylthio-3-ethylazetidin-2-on-1-yl)-3-phenoxy-3-trimethylacetylthiopropenate in dichloromethane at −20° was added a solution of 8.4 mmol of chlorine in carbon tetrachloride. After 30 minutes the mixture was warmed to room temperature, evaporated in vacuo, and the residual oil was chromatographed over silica gel. Elution with hexane-ethane acetate mixtures afforded 1.782 g of the title compound as a pale yellow foam (78% of the theoretical yield).

$\nu_{max}$ (CHCl$_3$) = 1784 cm$^{-1}$.

$\delta$(CDCl$_3$) 0.80–1.42 (12H, m, C(CH$_3$)$_3$, CH$_2$—CH$_3$), 1.56–2.15 (2H, m, CH$_2$CH$_3$), 3.00–3.80 (1H, m, 3-H), 5.30 (2H, s, CO$_2$CH$_2$), 5.71 6.17 (1H, 2d, J$_{trans}$ 1.5 Hz, J$_{cis}$ 3 Hz, 4-H), 6.86–8.37

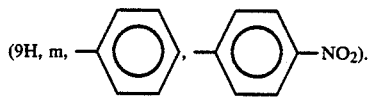

EXAMPLE 11

4-Nitrobenzyl 6-ethyl-7-oxo-3-phenoxy-4-thia-1-azabicyclo[3,2,0]hept-2-ene-2-carboxylate To a stirred solution of 0.416 g of 4-nitrobenzyl 2-(4-chloro-3-ethylazetidin-2-on-1-yl)-3-phenoxy-3-trimethylacetylthiopropenate in dioxan-water (9:1 v/v) at 5°, were added 104 mg of imidazole. After 30 minutes at 5° the mixture was warmed to room temperature, and then partitioned between ethyl acetate and water. The organic layer was separated, was washed with water, with aqueous citric acid, with water, with saturated sodium bicarbonate, and with brine, was dried over MgSO4, and then evaporated in vacuo to dryness. Chromatography over silica gel and elution with ethyl acetate-hexane mixtures afforded 216 mg of the title compound (67%) as a yellow foam.

$\nu_{max}$ = 1790 cm$^{-1}$, 1800 (sh) cm$^{-1}$.

$\delta$(CDCl$_3$) 0.80–1.42 (3H, m, CH$_2$CH$_3$), 1.56–2.20 (2H, m, CH$_2$CH$_3$), 3.53–4.05 (1H, m, 6-H), 5.35 (2E, q, CO$_2$CH$_2$), 5.36, 5.75 (1H, 2d, J$_{trans}$ 1.5 Hz, J$_{cis}$ 4 Hz, 5-H), 7.00–8.29

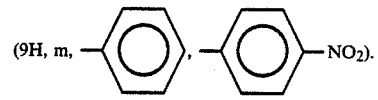

EXAMPLE 12

Sodium 6-ethyl-3-phenoxy-7-oxo-4-thia-1-azabicyclo[3,2,0]hept-2-ene-2-carboxylate A mixture of a solution of 306 mg of 4-nitrobenzyl 6-ethyl-3-phenoxy-7-oxo-4-thia-1-azabicyclo[3,2,0]hept-2-ene-2-carboxylate in dioxan and 60 mg of sodium bicarbonate in water, and 10% palladium/charcoal was hydrogenated at 50 psi at 25° for 60 minutes. The mixture was then filtered through Celite, and lyophilised to yield 216 mg of the title compound as a pale yellow crystalline solid (96% of the theoretical yield).

EXAMPLE 13

3(S)-{1(R)-Dimethyl(2-methylprop-2-yl)silyloxyethyl}-4(R)-ethylthioazetidin-2-one To a stirred solution of 2.03 g of sodium hydroxide in 70 ml of water at 0° C. under an argon atmosphere were added 3.94 g of ethane thiol. After 30 minutes stirring, a solution of 12.6 g of 3(S)-{1(R)-dimethyl(2-methylprop-2-yl)silyloxyethyl}-4-acetoxyazetidin-2-one in 200 ml of methanol was added. The mixture was warmed to room temperature and, after 90 minutes, was partitioned between ethyl acetate and water. The aqueous layer was further washed with ethyl acetate. The combined organic layers were backwashed with brine, dried over sodium sulphate, and evaporated to dryness. 6.9 g of the title product were obtained. Yield: 54%

$\nu_{max}$ (CDCl$_3$) 1765 cm$^{-1}$.

$\delta$(CDCl$_3$) 0.10 (6H, s); 0.90 (9H, s); 1.26 (3H, d, J=6 Hz), 1.33 (3H, t, J=7 Hz), 2.68 (2H, q, J=7 Hz), 3.16 (1H, m), 4.1–4.3 (1H, m), 4.85 (1H, d, J=2 Hz), 6.78 (1H, broad s).

EXAMPLE 14

Methyl 2-[3(S)-{1(R)-dimethyl(2-methylprop-2-yl)silyloxyethyl}-4(R)-ethylthio-azetidin-2-on-1-yl]acetate To a stirred solution of 6.9 g of 3(S)-{1(R)-dimethyl(2-methylprop-2-yl)silyloxyethyl}-4(R)-ethylthioazetidin-2-one in 150 ml of dry dimethylformamide were added 13.15 g of finely ground anhydrous potassium, carbonate and 2.82 ml of methyl bromoacetate. After 24 hours, the mixture was filtered and then partitioned between ethyl acetate and water. The aqueous layer was adjusted to pH2 by dropwise addition of dilute hydrochloric acid, and then back-extracted with ethyl acetate. The combined organic layers were washed with water, dried over sodium sulphate, and evaporated in vacuo to give an orange oil, which was chromatographed over silica gel. Elution with ethyl acetate/hexane mixtures afforded 6.37 g of the title compound as a pale yellow oil. Yield: 72%.

$\nu_{max}$(CDCl$_3$) 1749 (ester) and 1760 ($\beta$-lactam) cm$^{-1}$.

$\delta$(CDCl$_3$) 0.06 (6H, s), 0.86 (9H, s), 1.3 (6H, m), 2.58 (2H, q) J=6 Hz), 3.12 (1H, dd, J=2 Hz and 4 Hz), 3.70 (3H, s), 3.93 (2H, dd, J gem=17 Hz), 4.3 (1H, m), 4.92 (1H, d, J=2 Hz).

EXAMPLE 15

4-Nitrobenzyl 2-[3(S)-{1(R)-dimethyl-(2-methylprop-2-yl)-silyloxyethyl}-4(R)-ethylthio-azetidin-2-on-1-yl]-acetate To a solution of 6.37 g of methyl 2-[3(S)-{1(R)-dimethyl(2-methylprop-2-yl)silyloxyethyl}-4(R)-ethylthio-azetidin-2-on-1-yl]acetate in 25 ml of 95% ethanol was added a solution of 1.16 g of potassium hydroxide in 25 ml of 95% ethanol. After 15 minutes, the mixture was evaporated in vacuo to dryness. The product was dissolved immediately in 25 ml of dimethylacetamide, and 4.24 g of solid 4-nitrobenzyl bromide were added with vigorous stirring. After 60 minutes, the mixture was partitioned between ethyl acetate and water. The separated aqueous layer was washed with further ethyl acetate; the combined organic layers were backwashed with water, then with brine, and were then dried over sodium sulphate and evaporated in vacuo to afford an orange oil. Chromatography over silica gel, eluting with ethyl acetate/hexane mixtures afforded the title compound as a pale yellow, viscous oil. Yield: 6.18 g, 80%.

$\nu_{max}$(CDCl$_3$) 1765 ($\beta$-lactam) and 1755 (ester)cm$^{-1}$.

$\delta$(CDCl$_3$) 0.05 (3H, s), 0.08 (3H, s), 0.88 (9H, s), 1.25 (3H, t, J=7 Hz), 1.28 (3H, d, J=6 Hz), 2.58 (2H, q, J=7 Hz), 3.18 (1H, dd, J=2 Hz and 4 Hz), 4.05 (2H, dd, Jgem=18 Hz), 4.1–4.3 (1H, m), 4.93 (1H, d, J=2 Hz).

EXAMPLE 16

4-Nitrobenzyl 2-[3(S)-{1(R)-dimethyl-(2-methylprop-2-yl)-silyloxyethyl}-4(R)-ethylthio-azetidin-2-on-1-yl]-3-(4-methylthiophenoxy)-3-trimethylacetylthio-propenate.

To a stirred solution of 2.0 g of 4-nitrobenzyl 2-[3(S)-{1(R)-dimethyl-(2-methylprop-2-yl)silyloxyethyl}-4(R)-ethylthio-azetidin-2-on-1-yl]-acetate and 1.123 g of 4-(mercaptomethyl)phenoxy chlorothionoformate in dry tetrahydrofuran at $-100°$ C. under argon was added a solution of a mixture of 2.35 ml of hexamethyldisilazine and 6.64 ml of a 1.55 molar hexane solution of butyllithium in dry tetrahydrofuran. The mixture was stirred at $-100°$ for 30 minutes and at $-40°$ for 30 minutes, and 1.05 ml of trimethylacetyl chloride were added. The mixture was allowed to warm to room temperature and was stirred for 2 hours. Acetic acid was then added and the mixture was partitioned between ethyl acetate and water. The organic layer was washed with citric acid, with water, with sodium bicarbonate, with brine, and was then dried over magnesium sulphate and evaporated to dryness. Chromatography over silica gel, eluting with hexane/ethyl acetate mixtures, afforded 2.06 g of the title compound as a yellow oil. Yield: 65%.

$\nu_{max}$ (CDCl$_3$)=1764 cm$^{-1}$.

$\delta$(CDCl$_3$) 0.06 (6H, s), 0.80, 0.87 (9H, 2s), 1.0, 1.09 (9H, 2s), 1.23 (3H, t, J=7 Hz), 1.26 (3H, d, J=6 Hz), 2.42 (3H, s), 2.64 (2H, q, J=7 Hz), 3.20 (1H, dd, J=2 Hz and 4 Hz), 4.00–4.40 (1H, m), 5.30 (3H, bs), 6.73–7.31 (4H, m), 7.35–8.28 (4H, m).

EXAMPLE 17

4-Nitrobenzyl 2-[4(R)-ethylthio-3(S)-{1(R)-hydroxyethyl}azetidin-2-on-1-yl]-3-(4-methylthiophenoxy)-3-trimethylacetylthio-propenate To a stirred solution of 2.06 g of 4-nitrobenzyl 2-[3(S)-{1(R)-dimethyl-(2-methylprop-2-yl)silyloxyethyl}-4(R)-ethylthio-azetidin-2-on-1-yl]-3-(4-methylthiophenoxy)-3-trimethylacetylthio-propenate in tetrahydrofuran at room temperature were added 2 ml of water and 22 mmol of concentrated hydrochloric acid. The mixture was stirred for 28 hours until T.L.C. analysis showed the reaction to be complete. The mixture was partitioned between ethyl acetate and water, the organic layer was washed with sodium bicarbonate and brine, dried over MgSO$_4$ and evaporated to dryness. Chromatography over silica gel and elution with hexane-ethyl acetate mixtures afforded the title compound (1.21 g, 70%) as a yellow foam.

The product is isolated as a mixture of E and Z isomers, observed as double peaks in the nmr spectrum.

$\nu_{max}$ (CHCl$_3$)=1762 cm$^{-1}$.

$\delta$(CDCl$_3$) 1.02, 1.13 (9H, 2s), 1.28 (3H, t, J=7 Hz), 1.30 (3H, d, J=6 Hz), 2.44 (3H, s), 2.76 (2H, q, J=7 Hz), 3.24 (1H, dd, J=2 Hz and 4 Hz), 3.90–4.38 (1H, m), 5.23 (1H, d, J=2 Hz), 5.26 (2H, s), 6.74–7.20 (4H, m), 7.27–8.23 (4H, m).

EXAMPLE 18

4-Nitrobenzyl 2-[4(R)-chloro-3(S)-{1(R)-hydroxyethyl}azetidin-2-on-1-yl]-3-(4-methylthiophenoxy)-3-trimethylacetylthio-propenate.

To a stirred solution of 1 g of 4-nitrobenzyl 2-[4(R)-ethylthio-3(S)-{1(R)-hydroxyethyl}-azetidin-2-on-1-yl]-3-(4-methylthiophenoxy)-3-trimethylacetylthio-propenate in dichloromethane at $-40°$ was added a solution of 1.6 mmol of chlorine in carbon tetrachloride. After 30 minutes the reaction was warmed to room temperature and evaporated to dryness. Chromatography over silica gel and elution with hexane-ethyl acetate mixtures afforded the title compound as a pale yellow foam (0.66 g, 68%).

$\nu_{max}$ =1783 cm$^{-1}$.

$\delta$(CDCl$_3$) 1.06, 1.09 (9H, 2s), 1.40 (3H, d, J=6 Hz), 2.44 (3H, s), 3.52 (1H, dd, J=4 Hz and 9 Hz), 3.98–4.58 (1H, m), 5.30 (2H, s), 6.03, 6.17 (1H, 2d, J=4 Hz), 6.72–7.33 (4H, m), 7.38–8.32 (4H, m).

E and Z isomers are separable by chromatography.

EXAMPLE 19

4-Nitrobenzyl 5(R), 6(S)-{1(R)-hydroxyethyl}-3-(4-methylthiophenoxy)-7-oxo-4-thia-1-azabicyclo[3,2,0]hept-2-ene-2-carboxylate To a stirred solution of 0.342 g of 4-nitrobenzyl 2-[4(R)-chloro-3(S)-{1(R)-hydroxyethyl}-azetidin-2-on-1-yl]-3-(4-methylthiophenoxy)-3-trimethylacetylthio-propenate in dioxan-water (9:1 v/v) at $+5°$ were added 1.12 mmol of imidazole. After 30 minutes at $+5°$ the reaction mixture was warmed to room temperature and partitioned between ethyl acetate and water. The organic layer was washed with citric acid, with water, with saturated sodium bicarbonate and with brine, was dried over MgSO$_4$ and was then evaporated in vacuo to dryness. Chromatography over silica gel and elution with hexane-ethyl acetate mixtures afforded the title compound (0.133 g, 49%) as a pale yellow foam.

$\nu_{max}$ (CHCl$_3$)=1786, 1790 (sh), 1797 (sh) cm$^{-1}$.

δ(CDCl$_3$) 1.30 (3H, d, J=6 Hz), 2.46 (3H, s), 3.68 (1H, dd, J=1.5 Hz and 6 Hz), 3.88–4.33 (1H, m), 5.29 (2H, q), 5.56 (1H, d, J=1.5 Hz), 6.90–7.29 (4H, m), 7.31–8.20 (4H, m).

EXAMPLE 20

4-Nitrobenzyl 5(R), 6(S)-(1(R)-hydroxyethyl)-3-(4-methylsulphinylphenoxy)-7-oxo-4-thia-1-azabicyclo[3,2,0]hept-2-ene-2-carboxylate To a stirred solution of 0.28 g of 4-nitrobenzyl 5(R), 6(S)-{1(R)-hydroxyethyl}-3-(4-methylthiophenoxy)-7-oxo-4-thia-1-azabicyclo[3,2,0]hept-2-en-2-carboxylate in ethyl acetate at −78° was added a solution of 0.57 mmol of m-chloroperoxybenzoic acid in ethyl acetate. After 30 minutes the reaction mixture was warmed to room temperature and washed with saturated sodium bicarbonate, with brine, dried over MgSO$_4$, and then evaporated to dryness. Chromatography over silica gel and elution with hexaneethyl acetate mixtures afforded the title compound (0.19 g, 66%) as a white foam.

$\nu_{max}$ (CHCl$_3$)=1790, 1797 cm$^{-1}$.

δ(CDCl$_3$) 1.35 (3H, d, J=6 Hz), 2.73 (3H, s), 3.81 (1H, dd, J=1.5 Hz and 6 Hz), 3.90–4.37 (1H, m), 5.31 (2H, q), 5.74 (1H, d, J=1.5 Hz), 7.15–7.52 (4H, m), 7.55–8.27 (4H, m).

EXAMPLE 21

Sodium 5(R), 6(S)-(1(R)-hydroxyethyl)-3-(4-methylsulphinylphenoxy)-7-oxo-4-thia-1-azabicyclo[3,2,0]-hept-2-en-2-carboxylate A mixture of a solution of 65 mg of 4-nitrobenzyl 5(R), 6(S)-(1(R)-hydroxyethyl)-3-(4-methylsulphinylphenoxy)-7-oxo-4-thia-1-azabicyclo[3,2,0]hept-2-en-2-carboxylate in dioxan, and 11 mg sodium bicarbonate in water, and 10% palladium/charcoal was hydrogenated at 50 p.s.i. until T.L.C. analysis indicated complete reaction. The mixture was filtered through Celite (Trade Mark) and lyophilized to yield 42 mg of the title compound (83%) as a crystalline solid.

EXAMPLE 22

4-Nitrobenzyl 5(R), 6(S)-{1(R)-hydroxyethyl}-3-(4-methylsulphonyl-phenoxy)-7-oxo-4-thia-1-azabicyclo[3,2,0]hept-2-ene-2-carboxylate 20 mg of the above compound were obtained by a procedure analogous to that described in Example 20 using 125 mg of 4-nitrobenzyl 5(R), 6(S)-{1(R)-hydroxyethyl}-3-(4-methylsulphinylphenoxy)-7-oxo-4-thia-1-azabicyclo[3,2,0]hept-2-ene-2-carboxylate and 0.25 mmol m-chloroperoxybenzoic acid.

δ(CDCl$_3$) 1.39 (3H, d, J=6 Hz), 2.97 (1H, bs), 3.09 (3H, s), 3.86 (1H, dd, J=1.5 Hz and 6 Hz), 4.00–4.51 (1H, m), 5.30 (2H, q), 5.73 (1H, d, J=1.5Hz), 7.13–8.32 (8H, m).

EXAMPLE 23

Sodium 5(R), 6(S)-{1(R)-hydroxyethyl}-3-(4-methylsulphonyl-phenoxy)-7-oxo-4-thia-1-azabicyclo[3,2,0]hept-2-ene-2-carboxylate 18 mg of the above compound were obtained from 20 mg of the corresponding 4-nitrobenzyl compound (see Example 22) by a procedure analogous to that described in Example 21, using 3.2 mg of sodium bicarbonate.

EXAMPLE 24

4-Nitrobenzyl 2-[3(S)-{1(R)-dimethyl-(2-methylprop-2-yl) silyloxyethyl}-4(R)-ethylthioazetidin-2-on-1-yl]-3-phenoxy-3-trimethylacetylthio propenoate.

400 mg of the above compound were obtained, as a yellow oil, by procedure analogous to that described in Example 16, using 500 mg of the azetidinone starting material defined in Example 16, 200 mg of phenyl chlorothionoformate, 700 μl of hexamethyldisilazane and 2 ml of n-butyllithium, and 260 μl of trimethylacetyl chloride.

δ(CDCl$_3$) 0.01 (6H, s), 0.80, 0.90 (9H, 2s), 1.0, 1.06 (9H, 2s), 1.25 (6H, m), 2.7 (2H, q J=7 Hz), 3.20 (1H, dd), 4.0→4.40 (1H, m), 5.30 (3H, bm), 6.8–7.5 (5H, m), 7.5–8.4 (4H, m).

EXAMPLE 25

4-Nitrobenzyl 2[3(S)-{1(R)-hydroxyethyl}-4(R)-ethylthioazetidin-2-on-1-yl]-3-phenoxy-3-trimethylacetylthiopropenoate 0.19 g of the above compound were obtained from 0.390 g of the corresponding {1(R)-dimethyl-(2-methylprop-2-yl)silyloxyethyl} compound (see Example 24) by a procedure analogous to that described in Example 17, using 0.4 ml of water and 0.4 ml of concentrated hydrochloric acid.

δ(CDCl$_3$) 1.05, 1.10 (9H, 2s), 1.35 (5H, m), 2.70 (2H, q, J=7 Hz), 2.8 (1H, broad), 3.30 (1H, dd J=2 Hz+J=5 Hz), 4.03–4.46 (1H, m), 5.35 (3H, m), 6.94–7.50 (5H, m), 7.55–8.40 (4H, m).

EXAMPLE 26

4-Nitrobenzyl 2-[3(S)-{1(R)-hydroxyethyl}-4(S)-chloroazetidin-2-on-1-yl]-3-phenoxy-3-trimethylacetyl thiopropenoate To a stirred solution of 0.114 g of the 1(R)-hydroxyethylazetidinone derivative defined in Example 25 in CDCl$_3$ at −40° C. was added a solution of 0.2 mmol of chlorine in carbon tetrachloride and the solution was stirred for 1 hour. The reaction mixture was warmed to room temperature and evaporated to dryness. The product was used unpurified in the following step.

δ(CDCl$_3$) 1.03, 1.06 (9H, 2s), 1.40 (3H, m), 2.8 (1H, broad), 3.50 (1H, dd), 4.06–4.60 (1H, m), 5.30 (2H, s), 6.13 (1H, d, J=4 Hz), 6.90–7.40 (5H, m), 7.40–8.35 (4H, m).

EXAMPLE 27

4-Nitrobenzyl 5(R), 6(S)-{1(R)-hydroxyethyl}-3-phenoxy-7-oxo-4-thia-1-azabicyclo[3,2,0]hept-2-en-2-carboxylate 0.044 g of the above compound were obtained by a procedure analogous to that described in Example 19, using the unpurified product of Example 26 and 0.22 mmol of imidazole.

δ(CDCl$_3$) 1.30, 1.40 (3H, d, J=6 Hz), 2.0 (1H, broad), 3.76 (1H, dd J=1.5 Hz and 6 Hz), 3.96–4.43 (1H, m), 5.35 (2H, q), 5.63 (1H, d, J=1.5 Hz), 7.10–7.40 (5H, m), 7.50–8.30 (4H, m).

EXAMPLE 28

Sodium 5(R), 6(S)-{1(R)-hydroxyethyl}-3-phenoxy-7-oxo-4-thia-1-azabicyclo[3,2,0]hept-2-en-2-carboxylate 0.0237 g of the above compound were obtained from 0.031 g of the corresponding 4-nitrobenzyl carboxylate (see Example 27) by a procedure analogous to that described in Example 21, using 0.0061 g of sodium bicarbonate.

EXAMPLE 29

4-Nitrobenzyl 2[3(S)-{1(R)-dimethyl-(2-methylprop-2-yl)silyloxyethyl}-4(R)-ethylthioazetidin-2-on-1-yl]-3-(4-fluorophenoxy)-3-trimethylacetylthio propenoate 0.592 g of the above compound was obtained by a procedure analogous to that described in Example 16 using 0.5 g of the azetidinone starting material defined in Example 16, 171 μl of p-fluorophenyl chlorothionoformate, 0.67 ml of hexamethyldisilazine and 1.99 ml of n-butyllithium, and 261 μl of trimethylacetyl chloride.

$\nu_{max}$ (CDCl$_3$) 1763 cm$^{-1}$.

δ(CDCl$_3$) 0.06 (6H, s), 0.75, 0.80 (9H, 2s), 1.00, 1.06 (9H, 2s), 1.22 (3H, t, J=7 Hz), 1.25 (3H, t, J=6 Hz), 2.70 (2H, q, J≦7 Hz), 3.20 (1H, dd, J=2 Hz and 4 Hz), 4.00→4.40 (1H, m), 5.25 (3H, bs), 6.8→8.2 (8H, m).

EXAMPLE 30

4-Nitrobenzyl 2-[3(S)-{1(R)-hydroxyethyl}-4(R)-ethylthioazetidin-2-on-1-yl]-3-(4-fluorophenoxy)-3-trimethylacetylthiopropenoate 380 mg of the above compound were obtained from 590 mg of the corresponding {1(R)-dimethyl-(2-methylprop-2-yl)silyloxyethyl} compound (see Example 29) by a process analogous to that described in Example 17, using 1 ml of water and 1 ml of concentrated HCl.

$\nu_{max}$ (CDCl$_3$) 1761 cm$^{-1}$.

δ(CDCl$_3$) 1.02, 1.10 (9H, 2s), 1.20→1.30 (6H, m), 2.70 (2H, q, J=7 Hz), 2.8 (1H, broad), 3.28 (1H, dd, J=2 Hz and 4 Hz), 3.90→4.30 (1H, m), 5.22 (3H, bs), 6.85→8.20 (8H, m).

EXAMPLE 31

4-Nitrobenzyl 2-[3(S)-{1(R)-hydroxyethyl}-4(S)-chloroazetidin-2-on-1-yl]-3-(4-fluorophenoxy)-3-trimethylacetylthiopropenoate The above compound was obtained by a procedure analogous to that described in Example 26, using 378 mg of the 1(R)-hydroxyethylazetidinone derivative defined in Example 30, and a solution of 0.45 mmol of chlorine in 1.65 ml of carbon tetrachloride. The product was used in the subsequent reaction without purification.

δ(CDCl$_3$) 1.10, (9H, 2s), 1.30 (3H, t), 2.5 (1H, broad), 3.5 (1H, dd J=4 Hz and 9 Hz), 4.00 (1H, m), 5.30 (2H, s), 6.10 (1H, m), 6.80–8.30 (8H, m).

EXAMPLE 32

4-Nitrobenzyl 5(R), 6(S)-{1(R)-hydroxyethyl}-3-(4-fluorophenoxy)-7-oxo-4-thia-1-azabicyclo[3,2,0]hept-2-en-2-carboxylate 67 mg of the above compound were obtained by a procedure analogous to that described in Example 19 using 0.622 mmol of the unpurified product of Example 31 and 42.3 mg of imidazole.

$\nu_{max}$ (CDCl$_3$) 1786, 1790 (sh).

δ(CDCl$_3$) 1.32 (3H, d, J=6 Hz), 2.0 (1H, broad), 3.70 (1H, dd J=1.5 Hz and 6 Hz), 4.00–4.30 (1H, m), 5.30 (2H, q), 5.56 (1H, d, J=1.52 Hz), 6.90–8.30 (8H, m).

EXAMPLE 33

Sodium 5(R), 6(S)-{1(R)-hydroxyethyl}-3-(4-fluorophenoxy)-7-oxo-4-thia-1-azabicyclo[3,2,0]hept-2-en-2-carboxylate 46.3 mg of the above compound were obtained from 67 mg of the corresponding 4-nitrobenzyl carboxylate (see Example 32) by a procedure analogous to that described in Example 21 using 12.2 mg of sodium bicarbonate.

EXAMPLE 34

4-Nitrobenzyl 2-[3(S)-{1(R)-dimethyl-(2-methylprop-2-yl)silyloxyethyl}-4(R)-ethylthioazetidin-2-on-1-yl]-3-(4-chlorophenoxy)-3-trimethylacetylthio propenoate 600 mg of the above compound were obtained by a procedure analogous to that described in Example 16, using 500 mg of the azetidinone starting material defined in Example 16, 0.25 ml of p-chlorophenyl chlorothionoformate, 0.67 ml of hexamethyldisilazane and 1.99 ml of n-butyllithium, and 0.195 ml of trichloroacetyl chloride.

$\nu_{max}$ 1760 cm$^{-1}$.

δ(CDCl$_3$) 0.06 (6H, s), 0.8, 0.87, (9H, 2s), 1.05, 1.10 (9H, 2s), 1.20–1.40 (6H, m), 3.60 (2H, q, J=7 Hz), 3.20 (1H, dd, J=2 Hz and 4 Hz), 4.00–4.50 (1H, m), 5.20 (3H, bs), 6.70–8.30 (8H, m).

EXAMPLE 35

4-Nitrobenzyl 2-[3(S)-{1(R)-hydroxyethyl}-4(R)-ethylthioazetidin-2-on-1-yl]-3-(4-chlorophenoxy)-3-trimethylacetylthiopropenoate 290 mg of the above compound were obtained from 600 mg of the corresponding {1(R)-dimethyl-(2-methylprop-2-yl)silyloxyethyl} compound (see Example 34) by a procedure analogous to that described in Example 17 using 1 ml of water and 1 ml of concentrated HCl.

$\nu_{max}$ 1765 cm$^{-1}$.

δ(CDCl$_3$) 1.05, 1.10 (9H, 2s), 1.27 (6H, m), 2.70 (2H, q, J=7 Hz), 2.8 (1H, broad), 3.20 (1H, dd, J=2 Hz and 4 Hz), 3.90→4.40 (1H, m), 5.25 (3H, bs), 6.80→8.20 (8H, m).

EXAMPLE 36

4-Nitrobenzyl 2-[3(S)-{1(R)-hydroxyethyl}-4(S)-chloroazetidin-2-on-1-yl]-3-(4-chlorophenoxy)-3-trimethylacetylthiopropenoate The above compound was obtained by a process analogous to that described in Example 26 using 290 mg of the 1(R)-hydroxyethylazetidinone derivative defined in Example 35 and a solution of 0.45 mmol of chlorine in 1 ml of carbon tetrachloride. The product was used in the next reaction without purification.

δ(CDCl₃) 1.05, 1.10 (9H, 2s), 1.40 (3H, d, J=6 Hz), 2.5 (1H, broad), 3.50 (1H, m), 4.00→4.50 (1H, m), 5.22 (2H, s), 6.03, 6.15 (1H, 2d, J=4 Hz), 6.80→8.30 (8H, m).

EXAMPLE 37

4-Nitrobenzyl 5(R), 6(S)-{1(R)-hydroxyethyl}-3-(4-chlorophenoxy)-7-oxo-4-thia1-azabicyclo[3,2,0]hept-2-en-2-carboxylate 57 mg of the above compound were obtained by a procedure analogous to that described in Example 19, using 0.458 mmol of the unpurified product of Example 36, and 32 mg of imidazole.

$\nu_{max}$ 1787, 1790 (sh) cm⁻¹.

δ(CDCl₃) 1.30 (3H, d, J=6 Hz), 2.0 (1H, broad), 3.60 (1H, dd, J=1.5 Hz and 6 Hz), 3.90–4.40 (1H, m), 5.22 (2H, q), 5.55 (1H, d, J=1.5 Hz), 6.80–8.20 (8H, m).

EXAMPLE 38

Sodium 5(R), 6(S)-{1(R)-hydroxyethyl}-3-(4-chlorophenoxy)-7-oxo-4-thia-1-azabicyclo[3,2,0]hept-2-en-2-carboxylate 43 mg of the above compound were obtained from 57 mg of the corresponding 4-nitrobenzyl carboxylate (see Example 37) by a procedure analogous to that described in Example 21, using 10 mg of sodium bicarbonate.

EXAMPLE 39

4-Nitrobenzyl 2-[3(S)-{1(R)-dimethyl-(2-methylprop-2-yl)silyloxyethyl}-4(R)-ethylthioazetidin-2-on-1-yl]-3-(4-cyanophenoxy)-3-trimethylacetylthio propenoate 1.12 g of the above compound were obtained by a procedure analogous to that described in Example 16 using 1 g of the azetidinone starting material defined in Example 16, 0.63 g of p-cyanophenyl chlorothionoformate, 1.34 ml of hexamethyldisilazine and 3.98 ml of n-butyllithium, and 0.52 ml of trimethylacetyl chloride.

$\nu_{max}$ 1768 cm⁻¹.

NMR δ(CDCl₃) 0.06 (6H, s), 0.80, 0.87 (9H, 2s), 1.05, 1.10 (9H, 2s), 1.20 (6H, m), 2.70 (2H, q, J=7 Hz), 3.22 (1H, dd, J=2 Hz and 4 Hz), 3.90–4.40 (1H, m), 5.30 (3H, bs), 6.88–8.30 (8H, m).

EXAMPLE 40

4-Nitrobenzyl 2-[3(S)-{1(R)-hydroxyethyl}-4(R)-ethylthioazetidin-2-on-1-yl]-3-(4-cyanophenoxy)-3-trimethylacetylthiopropenoate 185 mg of the above compound were obtained from 325 mg of the corresponding {1(R)-dimethyl-(2-methylprop-2-yl)silyloxyethyl} compound (see Example 39) by a procedure analogous to that described in Example 17, using 0.55 ml of water and 0.55 ml of concentrated hydrochloric acid.

$\nu_{max}$ 1765 cm⁻¹.

δ(CDCl₃) 1.05, 1.10 (9H, 2s), 1.30 (6H, m), 2.61 (2H, q, J=7 Hz), 2.8 (1H, broad), 3.16 (1H, dd, J=2 Hz and 4 Hz), 3.91–4.50 (1H, m), 5.30 (3H, bs), 6.90–8.3 (8H, m).

EXAMPLE 41

4-Nitrobenzyl 2-[3(S)-{1(R)-hydroxyethyl}-4-(S)-chloroazetidin-2-one-1-yl]-3-(4-cyanophenoxy)-3-trimethylacetylthiopropenoate The above compound was obtained by a process analogous to that described in Example 26 using 340 mg of the 1(R)-hydroxyethylazetidinone derivative defined in Example 40 and a solution of 0.676 mmol of chlorine in 0.81 ml of carbon tetrachloride. The product was used in the next reaction without purification.

$\nu_{max}$ 1785 cm⁻¹.

δ(CDCl₃) 1.06, 1.09 (9H, 2s), 1.35 (3H, d, J=6 Hz), 2.5 (1H, broad), 3.50 (1H, dd, J=4 Hz and 9 Hz), 3.95–4.40 (1H, m), 5.35 (2H, s), 6.03, 6.17, (1H, 2d, J=4 Hz), 6.90→8.4 (8H, m).

EXAMPLE 42

4-Nitrobenzyl 5(R), 6(S)-{1(R)-hydroxyethyl}-3-(4-cyanophenoxy)-7-oxo-4-thia-1-azabicyclo[3,2,0]hept-2-en-2-carboxylate 89 mg of the above compound were obtained by a procedure analogous to that described in Example 19, using 350 mg of the unpurified product of Example 41 and 45 mg of imidazole.

δ(CDCl₃) 1.30 (3H, d, J=6 Hz), 2.55 (1H, broad), 3.8 (1H, dd, J=1.5 Hz and 6 Hz), 4.23 (1H, m), 5.25 (2H, q), 5.70 (1H, d, J=1.5 Hz), 7.15–8.20 (8H, m).

EXAMPLE 43

Potassium 5(R), 6(S)-{1(R)-hydroxyethyl}-3-(4-cyanophenoxy)-7-oxo-4-thia-1-azabicyclo[3,2,0]hept-2en-2-carboxylate 67 mg of the above compound were obtained from 100 mg of the corresponding 4-nitrobenzyl carboxylate (see Example 42) by a procedure analogous to that described in Example 21, using 21 mg of potassium bicarbonate.

δ(D₂O) 2.00 (3H, d, J=6 Hz), 4.60 (1H, dd, J=1.5 Hz and 6 Hz), 4.81 (1H, m), 5.40H₂O (from D₂O), 6.38 (1H, d, J=1.5 Hz), 7.8–8.4 (4H, m).

EXAMPLE 44

4-Nitrobenzyl 2-[3(S)-{1(R)-dimethyl-(2-methylprop-2-yl)silyloxyethyl}-4(R)-ethylthioazetidin-2-on-1-yl]-3-(4-tolyloxy)-3-trimethylacetylthio-propenoate 2.0 g of the above compound were obtained by a procedure analogous to that described in Example 16, using 2.0 g of 4-nitrobenzyl 2-[3(S)-{1(R)-dimethyl-(2-methylprop-2-yl)silyloxyethyl}-4(R)-ethylthio-azetidin-2-on-1-yl]acetate, 2.35 ml of hexamethyldisilazane, 0.873 g of 4-tolyloxychlorothionoformate, 10.63 mmol of n-butyllithium, and 0.78 ml of trimethylacetyl chloride.

δ(CDCl₃) 0.07 (6H, s), 0.80, 0.87 (9H, 2s), 1.0, 1.10 (9H, 2s), 1.24 (3H, t, J=7 Hz), 1.28 (3H, d, J=6 Hz), 1.33 (3H, s), 2.75 (2H, q, J=7 Hz), 3.20 (1H, dd, J=2 Hz and 4 Hz), 3.90–4.36 (1H, m), 5.23 (3H, bs), 6.60–7.14 (4H, m), 7.34–8.27 (4H, m).

EXAMPLE 45

4-Nitrobenzyl 2-[3(S)-{1(R)-hydroxyethyl}-4(R)-ethylthio azetidin-2-on-1-yl]-3-(4-tolyloxy)-3-trimethylacetylthio-propenoate 258 mg of the above compound were obtained from 502 mg of the corresponding {1(R)-dimethyl-(2-methylprop-2-yl)silyloxyethyl} compound (see Example 44) by a procedure analogous to that described in Example 17 using 5.5 mmoles of 6M HCl.

δ(CDCl$_3$) 1.01, 1.09 (9H, 2s), 1.30 (3H, t, J=7 Hz), 1.33 (3H, d, J=6 Hz), 2.33 (3H, s), 2.64 (2H, q, J=7 Hz), 3.22 (1H, dd, J=2 Hz and 4 Hz), 4.00–4.40 (1H, m), 5.22 (1H, d, J=2 Hz), 5.26 (2H, s), 6.73–7.18 (4H, m), 7.32–8.20 (4H, m).

EXAMPLE 46

4-Nitrobenzyl 2-[3(S)-{1R-hydroxyethyl}-4(S)-chloroazetidin-2-on-1yl]-3-(4-tolyloxy)-3-trimethyl-3-acetylthiopropenoate The above compound was obtained by a process analogous to that described in Example 26 using 0.213 g of the 1(R)hydroxyethylazetidinone derivative defined in Example 45 and a solution of 0.365 mmol chlorine in carbon tetrachloride. The product was used in the next reaction without purification.

δ(CDCl$_3$) 1.06, 1.10 (9H, 2s), 1.38 (3H, d, J=6 Hz), 2.33 (3H, s), 2.81 (1H, bs), 3.60 (1H, dd, J=4 Hz, 9 Hz), 4.02–4.47 (1H, m), 5.33 (2H, s), 6.11, 6.24 (1H, 2d, J=4 Hz), 6.72–8.30 (8H, m).

EXAMPLE 47

4-Nitrobenzyl 5(R), 6(S)-{1(R)-hydroxyethyl}-3-(4-tolyloxy)-7-oxo-4-thia-1-azabicyclo[3,2,0]hept-2-en-2-carboxylate 89 mg of the above compound were obtained by a procedure analogous to that described in Example 19 using 3 mmol of the unpurified product of Example 46 and 49 mg of imidazole.

ν$_{max}$ (CHCl$_3$)=1788 cm$^{-1}$.

δ(CDCl$_3$) 1.31 (3H, d, J=6 Hz), 2.36 (3H, s), 2.60 (1H, bs), 3.68 (1H, dd, J=1.5 Hz, and 6 Hz), 4.00–4.40 (1H, m), 5.33 (2H, q), 5.57 (1H, d, J=1.5 Hz), 7.12 (4H, s), 7.36–8.29 (4H, m).

EXAMPLE 48

Sodium 5(R), 6(S)-{1(R)-hydroxyethyl}-3-(4-tolyloxy)-7-oxo-4-thia-1-azabicyclo[3,2,0]hept-2-en-2-carboxylate 69 mg of the above compound were obtained from 150 mg of the corresponding 4-nitrobenzyl carboxylate (see Example 47) by a procedure analogous to that described in Example 21, using 0.33 mmol of sodium bicarbonate.

EXAMPLE 49

4(R)-Allylthio-3(S)-[1(R)-{dimethyl-(2-methylprop-2-yl)silyloxy}ethyl]-azetidin-2-one To a stirred solution of 1.14 ml of allyl mercaptan (70%) and 0.4 g of sodium hydroxide in 25 ml of water under an argon atmosphere was added a solution of 2.87 g of 4-acetoxy-3(S)-[1(R)-{dimethyl-(2-methylprop-2-yl)silyloxy}ethyl]-azetidin-2-one in 10 ml of methanol. After 30 minutes, the mixture was partitioned between dichloromethane and water. The separated organic layer was washed with water, dried over MgSO$_4$, evaporated to dryness, and then chromatographed on silica gel. Elution with ethyl acetate-hexane mixtures afforded 1.8 g of the title compound as white crystals.

ν$_{max}$ (CDCl$_3$) 3420, 1767 cm$^{-1}$.

δ (CDCl$_3$) 0.05 (6H, s), 0.88 (9H, s), 1.20 (3H, d, J 6 Hz), 2.9–3.2 (3H, m), 3.9–4.3 (1H, m), 4.84 (1H, d, J$_{3,4}$ 2 Hz), 4.95–6.3 (3H, m), 7.28 (1H, broad s).

EXAMPLE 50

Methyl 2-(4(R)-allylthio-3(S)-[1(R)-{dimethyl-(2-methylprop-2-yl)silyloxy}ethyl]azetidin-2-on-1-yl)acetate To a stirred solution of 1.76 g of 4(R)-allylthio-3(S)-[1(R)-{dimethyl-(2-methylprop-2-yl)silyloxy}ethyl]azetidin-2-one in 60 ml dry DMF were added 3.52 g of finely ground K$_2$CO$_3$ and 0.6 ml of methyl bromoacetate. After 18 hours, the mixture was filtered and then partitioned between ethyl acetate and water. The separated organic layer was washed with water and dried over MgSO$_4$. Evaporation in vacuo afforded a crude product which was chromatographed on silica gel. Elution with ethyl acetate-hexane mixtures afforded 1.56 g of the title compound as a pale yellow oil.

ν$_{max}$ CDCl$_3$ 1753, and 1768 cm$^{-1}$.

δ (CDCl$_3$) 0.06 (6H, s), 0.86 (9H, s), 1.23 (3H, d J 6.5 Hz), 3.2 (3H, m), 3.70 (3H, s), 3.6–4.3 (3H, m), 4.87 (1H, d J∼2 Hz), 4.9–6.3 (3H, m).

EXAMPLE 51

4-Nitrobenzyl 2-(4(R)-allylthio-3(S)-[1(R)-{dimethyl-(2-methylprop-2-yl)-silyloxy}ethyl]-azetidin-2-on-1-yl)acetate To a stirred solution of 3.04 g of 85% pure KOH in 80 ml of 95% ethanol was added a solution of 16 g methyl 2-(4(R)-allylthio-3(S)-[1(R)-{dimethyl-(2-methylprop-2-yl)silyloxy}ethyl]azetidin-2-on-1-yl)acetate. After 10 minutes the mixture was evaporated to about one fifth of its volume; 100 ml of dimethyl acetamide were added, followed by a solution of 9.25 g of 4-nitrobenzyl bromide in 50 ml dimethylacetamide. After 1 hour, the mixture was partitioned between 0.01M HCl and ethyl acetate. The separated organic layers were washed with 0.01M HCl, with water, with cold saturated NaHCO$_3$ and with brine, were dried and evaporated. The crude product was chromatographed over silica gel; elution with ethyl acetate-hexane mixtures afforded 19.5 g of the title compound.

ν$_{max}$ (CDCl$_3$) 1755 and 1769 cm$^{-1}$.

δ (CDCl$_3$) 0.07 and 0.09 (6H, two singlets), 0.88 (9H, s), 1.25 (3H, d J 6 Hz), 3.2 (3H, m), 3.7–4.5 (3H, m), 4.95 (1H, d J 2 Hz), 4.9–6.3 (5H, m), 7.5–8.35 (4H, m).

EXAMPLE 52

4-Nitrobenzyl 2-[2(S)-{1(R)-dimethyl-(2-methylprop-2-yl)silyloxyethyl}-4-(R)-allylthioazetidin-2-on-1-yl]-3-(4-chlorophenoxy-3-trimethylacetylthio-propenoate 670 mg of the above compound were obtained by a procedure analogous to that described in Example 16, using 1 g of 4-nitrobenzyl 2-[3(S)-{1(R)-dimethyl-(2-methylprop-2-yl)silyloxyethyl}4(R)-allylthioazetidin-2-on-1-yl]acetate, 0.32 ml of 4-chlorophenyl chlorothonoformate, 0.95 ml of hexamethyldisilazane and 2.28 ml of 1.6M n-butyllithium, and 0.4 ml of pivoloyl chloride; and 1.0 ml of glacial acetic acid.

$\nu_{max}$ (CDCl$_3$) 1733 and 1759 cm$^{-1}$.

δ (CDCl$_3$) 0.04 (6H, s), 0.83 (9H, s), 1.03 and 1.06 (9H, two singlets), 1.23 (3H, d J∼7 Hz), 3.0–3.4 (3H, m), 4.0–4.3 (1H, m), 4.9–6.0 (6H, m), 6.8–8.4 (8H, m).

EXAMPLE 53

4-Nitrobenzyl 2-[3(S)-{1(R)-dimethyl-(2-methylprop-2-yl)silyloxyethyl}-4(R)-chloroazetidin-2-on-1-yl]-3-(4-chlorophenoxy)-3-trimethylacetylthio-propenoate The above compound was obtained by a process analogous to that described in Example 26 using 73 mg of the corresponding 4(R)-allylthioazetidinone derivative (see Example 51) and a solution of 1.24 mmol of chlorine in 0.12 ml of carbon tetrachloride.

$\nu_{max}$ 1788 cm$^{-1}$.

NMR δ(CDCl$_3$) 0.06 (6H, s), 0.90, 0.91 (9H, 2s), 1.05, 1.10 (9H, 2s), 1.40 (3H, d, J=6 Hz), 3.40 (1H, dd 1.5 Hz and 8 Hz), 4.00–4.40 (1H, m), 5.40 (2H, s), 6.1 (1H d J=1.5 Hz), 6.8→8.5 (8H, m).

EXAMPLE 54

4-Nitrobenzyl 5(S),6(S)-{1(R)-dimethyl-(2-methylprop-2-yl)silyloxyethyl}-3-(4-chlorophenoxy)-7-oxo-4-thia-1-azabicyclo[3,2,0]hept-2-en-2-carboxylate 108 mg of the above compound were obtained by a procedure analogous to that described in Example 19, using 200 mg of the unpurified product of Example 53 and 24.8 mg of imidazole.

$\nu_{max}$ 1792, 1800 (sh).

δ (CDCl$_3$) 0.06 (6H, s), 0.90, 0.92, (9H, 2s), 1.38 (3H, d, J=7 Hz), 3.80–4.8 (2H, m), 5.22 (2H, q), 5.65 (1H, d, J=4 Hz), 6.90–8.50 (8H, m).

EXAMPLE 55

4-Nitrobenzyl 5(S)-3-(4-chlorophenoxy)-6(S)-[1(R)-hydroxyethyl]-7-oxo-4-thia-1-aza-bicyclo[3,2,0]hept-2-ene-2-carboxylate To a solution of 108 mg of 4-nitrobenzyl 5(S)-3-(4-chlorophenoxy)-6(S)-{1(R)-{dimethyl-[2-methylprop-2-yl)silyloxy}ethyl}-7-oxo-4-thia-1-azabicyclo[3,2,0-]hept-2-ene-2-carboxylate in 54.9 μl acetic acid at room temperature were added 54 μl of a 1 molar THF solution of tetrabutylammonium fluoride. After the mixture had been stirred for 16 hours, it was partitioned between ethyl acetate and water; the organic layer was separated, was washed with water, with saturated NaHCO$_3$ solution, with brine, and was then dried over MgSO$_4$ and evaporated in vacuo. Chromatography over silica gel and elution with ethyl acetate-hexane mixtures afforded 33 mg of the title compound.

$\nu_{max}$ (CDCl$_3$) 1790 and 1800 cm$^{-1}$.

δ (CDCl$_3$) 1.40 (3H, d, J=7 Hz), 2.25 (1H, broad), 3.86 (1H, dd J=4 Hz and 10 Hz), 4.4 (1H, m), 5.30 (2H, AB, J=14 Hz), 5.70 (1H, d, J=4 Hz), 6.8–8.5 (8H, m).

EXAMPLE 56

Sodium 5R-3-(4-methylthiophenoxy)-6S-(1R-hydroxyethyl)-7-oxo-4-thia-1-azabicyclo[3,2,0]hept-2-ene-2-carboxylate 63 mg of above compound were obtained by a procedure analogous to that described in Example 21, using 84 mg of the corresponding 4-nitrobenzyl carboxylate (see Example 19) and 13 mg of sodium bicarbonate.

EXAMPLE 57

4-Nitrobenzyl 2-[3(S)-{1(R)-dimethyl(2-methylprop-2-yl)silyloxyethyl}-4(R)-ethylthio-azetidin-2-on-1-yl]-3-(2-fluorophenoxy)-3-trimethylacetylthio-propenate 840 mg of the above compound were obtained by a procedure analogous to that described in Example 16, using 1 g of the azetidinone starting material, 486 mg of 2-fluorophenoxy chlorothionoformate, 1.18 mls of hexamethylsilazone and 5.32 mmol of n-butyllithium, and 0.525 ml of trichloroacetyl chloride.

$\nu_{max}$ 1764 cm$^{-1}$.

δ(CDCl$_3$) 0.06 (6H, s), 0.81, 0.87 (9H, 2s), 0.97, 1.05 (9H, 2s), 1.15–1.33 (6H, m), 2.67 (2H, q, J=7 Hz), 3.22 (1H, dd, J=2 Hz and 4 Hz), 4.02–4.40 (1H, m), 5.30 (2H, s), 5.39 (1H, d, J=2 Hz), 6.90–8.27 (8H, m).

EXAMPLE 58

4-Nitrobenzyl 2-[4(R)-ethylthio-3(S)-{1(R)-hydroxyethyl}azetidin-2-on-1-yl]-3-(2-fluorophenoxy)-3-trimethylacetylthio-propenate 434 mg of the above compound were obtained from 830 mg of the corresponding {1(R)-dimethyl-(2-methylprop-2-yl)silyloxyethyl} compound (see Example 57) by a procedure analogous to that described in Example 17, using 0.85 ml of water and 0.85 ml of concentrated hydrochloric acid.

$\nu_{max}$ 1760 cm$^{-1}$.

δ (CDCl$_3$) 1.01, 1.09 (9H, 2s), 1.21–1.48 (6H, m) 2.65 (1H, bs), 2.68 (2H, q, J=7 Hz), 3.23 (1H, dd, J=2 Hz and 4 Hz), 4.02–4.40 (1H, m), 5.30 (3H, bs), 6.95–8.26 (8H, m).

EXAMPLE 59

4-Nitrobenzyl 2-[4(S)-chloro-3(S)-{1(R)-hydroxyethyl}azetidin-2-on-1-yl]-3-(2-fluorophenoxy)-3-trimethylacetylthio-propenate 233 mg of the above compound were prepared by a procedure analogous to that described in Example 26 using 434 mg of the 1(R)-hydroxyethyl azetidinone derivative defined in Example 58 and 0.78 mmol of chloride in 1.01 mls carbon tetrachloride.

$\nu_{max}$ 1780 cm$^{-1}$.

δ (CDCl$_3$) 1.0, 1.04 (9H, 2s), 1.20–1.55 (6H, m), 2.52 (1H, bs), 3.51 (1H, dd, J=4 Hz and 9 Hz), 3.95–4.48 (1H, m), 5.21 (2H, s), 5.98, 6.10 (1H, 2d, J=4 Hz), 6.87–8.15 (8H, m).

EXAMPLE 60

4-Nitrobenzyl 5(R)-3-(2-fluorophenoxy)-6(S)-{1(R)-hydroxyethyl}-7-oxo-4-thia-1-azabicyclo[3,2,0]hept-2-ene-2-carboxylate 58 mg of the above compound were obtained by a procedure analogous to that described in Example 19 using 233 mg of the product of Example 59 and 54 mg of imidazole.

$\nu_{max}$ 1790, 1795 (sh) cm$^{-1}$.

δ (CDCl$_3$) 1.37 (3H, d, J=6 Hz), 2.22 (1H, bs), 3.75 (1H, dd, J=1.5 Hz and 6 Hz), 4.05–4.50 (1H, m), 5.34 (2H, q), 5.62 (1H, d, J=1.5 Hz), 7.04–7.33 (4H, m), 7.39–8.22 (4H, m).

EXAMPLE 61

Potassium 5(R)-3-(2-fluorophenoxy)-6S-{1(R)-hydroxyethyl}-7-oxo-4-thia-1-azabicyclo[3,2,0]hept-2-ene-2-carboxylate 56 mg of the above compound were obtained by a procedure analogous to that described in Example 21, using 58 mg of the corresponding 4-nitrobenzyl carboxylate (see Example 60) and 13 mg of potassium bicarbonate.

EXAMPLE 62

4-Nitrobenzyl 2-[3(S)-{1(R)-dimethyl-(2-methylprop-2-yl)silyloxyethyl}-4(R)-ethylthioazetidin-2-on-1-yl]-3-(3-fluorophenoxy)-3-trimethylacetylthio-propenate 0.974 g of the above compound was obtained by a procedure analogous to that described in Example 16, using 1.0 g of 4-nitrobenzyl 2-[3(S)-{1(R)-dimethyl-(2-methylprop-2-yl)silyloxyethyl}-4(R)-ethylthioazetidin-2-on-1-yl]acetate, 1.34 ml of hexamethyldisilazane, 0.6 g of 3-fluorophenylchlorothionoformate, 6.38 mmol of n-butyllithium, and 0.53 ml of trimethylacetyl chloride.

$v_{max}$ (CDCl$_3$) 1763 cm$^{-1}$.

$\delta$ (CDCl$_3$) 0.06 (6H, s), 0.75, 0.80 (9H, 2s), 1.05, 1.10 (9H, 2s), 1.22 (3H, t, J=7 Hz), 1.25 (3H, t, J=6 Hz), 2.71 (2H, q), 3.22 (1H, dd), 4.0–4.5 (1H, m), 5.35 (3H, bs), 6.8→8.2 (8H, m).

EXAMPLE 63

4-Nitrobenzyl 2-[3(S)-{1(R)-hydroxyethyl}-4(R)-ethylthioazetidin-2-on-1-yl]-3-(3-fluorophenoxy)-3-trimethylacetylthiopropenate 0.516 g of the above compound was obtained from 0.97 g of the corresponding {(1(R)-dimethyl-(2-methylprop-2-yl)silyloxyethyl} compound (see Example 62) by a procedure analogous to that described in Example 17 using 2 ml of concentrated hydrochloric acid, 2 ml of water and 20 ml of tetrahydrofuran.

IR $v_{max}$ (CDCl$_3$) 1762 cm$^{-1}$.

$\delta$(CDCl$_3$) 1.06, 1.10 (9H, 2s), 1.20–1.30 (6H, m), 2.50 (1H, b), 2.70 (2H, q), 3.24 (1H, dd), 3.91→4.40 (1H, m), 5.30 (3H, bs), 6.70–8.20 (8H, m).

EXAMPLE 64

4-Nitrobenzyl 2-[3(S)-{1(R)-hydroxyethyl}-4(S)-chloroazetidin-2-on-1-yl]-3-(3-fluorophenoxy)-3-trimethylacetylthio-propenate 405 mg of the above compound were obtained by a process analogous to that described in Example 26 using 516 mg of the 1(R)-hydroxyethylazetidinone derivative defined in Example 63 and a solution of 0.912 mmol of chlorine in 1.2 ml of carbon tetrachloride. The product was used in the next reaction without purification.

$v_{max}$ (CDCl$_3$) 1782 cm$^{-1}$.

$\delta$(CDCl$_3$) 1.06, 1.10 (9H, 2s), 1.35 (3H, t), 2.5 (1H, b), 3.5 (1H, dd J=4 Hz and 9 Hz), 4.05 (1H, m), 5.30 (2H, s), 6.10 (1H, d, J=4 Hz), 6.80–8.30 (8H, m).

EXAMPLE 65

4-Nitrobenzyl 5(R),6(S)-{1(R)-hydroxyethyl}-3-(3-fluorophenoxy)-7-oxo-4-thia-1-azabicyclo[3,2,0]hept-2-ene-2-carboxylate 205 mg of the above compound were obtained by a procedure analogous to that described in Example 19 using 400 mg of the unpurified product of Example 64 and 56.2 mg of imidazole.

$v_{max}$ (CDCl$_3$) 1784 cm$^{-1}$ 1790 (sh) cm$^{-1}$.

$\delta$(CDCl$_3$) 1.32 (3H, d), 1.90 (1H, b), 3.70 (1H, dd J=1.5 H and 6 Hz), 4.00–4.30 (1H, m), 5.30 (2H, q), 5.56 (1H, d, J=1.5 Hz), 6.90–8.30 (8H, m).

EXAMPLE 66

Potassium 5(R),6(S)-{1(R)-hydroxyethyl}-3-(3-fluorophenoxy)-7-oxo-4-thia-1-azabicyclo[3,2,0]hept-2-ene-2-carboxylate 160 mg of the above compound were obtained from 200 mg of the corresponding 4-nitrobenzyl carboxylate (see Example 65) by a procedure analogous to that described in Example 21, using 43.4 mg of potassium bicarbonate.

EXAMPLE 67

Pivaloyloxymethyl 3-(3-fluorophenoxy)-6(S)-{1(R)-hydroxyethyl≡-7-oxo-4-thia-1-azabicyclo[3,2,0]hept-2-ene-2-carboxylate To a solution of 100 mg of potassium 3-(3-fluorophenoxy)-6(S)-{1(R)-hydroxyethyl}-7-oxo-4-thia-1-azabicyclo[3,2,0]hept-2-ene-2-carboxylate in 1 ml of dimethylformamide were added 98 $\mu$l of pivaloyloxymethyl iodide and the mixture was stirred at room temperature for 90 minutes. The mixture was partitioned between ethyl acetate and water, the organic layer was washed with water and brine, dried over magnesium sulphate and evaporated in vacuo to dryness. Chromatography over silica gel and elution with hexane-ethylacetate afforded 50 mg of the title compound as a yellow oil.

$\delta$(CDCl$_3$) 1.20 (9H, s), 1.34 (3H, d, J=6 Hz), 2.41 (1H, bs), 3.75 (1H, dd, J=1.5 Hz, 6 Hz), 4.27 (1H, m), 5.67 (1H, s), 5.86 (2H, q), 6.81–7.45 (4H, m).

EXAMPLE 68

4-Nitrobenzyl 2-[4(R)-ethylthio-3(S)-{1(R)-dimethyl-(2-methylprop-2-yl)silyoxyethyl}azetidin-2-on-1-yl]-3-(2-cyanophenoxy)-3-trimethylacetylthiopropenate 0.56 g of the above compound was obtained by a procedure analogous to that described in Example 16, using 1 g of 4-nitrobenzyl 2-[3(S)-{1(R)-dimethyl-(2-methylprop-2-yl)silyloxyethyl}-4(R)-ethylthioazetidin-2-on-1-yl]acetate, 1.34 ml of hexamethyldisilazane, 0.63 g of 2-cyanophenyl chlorothionoformate, 6.38 mmol of n-butyllithium, and 0.53 ml of trimethylacetyl chloride.

$v_{max}$ (CDCl$_3$) 1765 cm$^{-1}$.

$\delta$(CDCl$_3$) 0.07 (6H, s), 0.80, 0.87 (9H, 2s), 1.10, 1.15 (9H, 2s), 1.23 (3H t J=7 Hz), 1.26 (3H d J=6 Hz), 2.62 (2H, q), 3.25 (1H, d,d), 4.0–4.5 (1H, m), 5.40 (3H bs), 7.10–8.50 (8H, m).

EXAMPLE 69

4-Nitrobenzyl 2-[4(R)-ethylthio-3(S)-{1(R)-hydroxyethyl}azetidin-2-on-1-yl]-3-(2-cyanophenoxy)-3-trimethylacetylthiopropenate 0.220 g of the above compound was obtained from 0.560 g of the corresponding {1(R)-dimethyl-(2-methylprop-2-yl)silyloxyethyl} compound (see Example 68) by a procedure analogous to that described in Example 17 using 1.5 ml of concentrated hydrochloric acid, 1.5 ml of water and 20 ml of tetrahydrofuran.

$\nu_{max}$ (CDCl$_3$) 1763 cm$^{-1}$.

$\delta$(CDCl$_3$) 1.06, 1.10 (9H, 2s), 1.20–1.40 (6H, m), 2.50 (1H, b), 2.80 (2H, q), 3.24 (1H, dd), 4.0–4.40 (1H, m), 5.40 (3H, bs), 7.10–8.35 (8H, m).

EXAMPLE 70

4-Nitrobenzyl 2[4(S)-chloro-3(S)-{1(R)-hydroxyethyl}azetidin-2-on-1-yl]-3-(2-cyanophenoxy)-3-trimethylacetylthio-propenate 132 mg of the above compound were obtained by a process analogous to that described in Example 26 using 190 mg of the 1(R)-hydroxyethylazetidinone derivative defined in Example 69 and a solution of 0.33 mmol of chlorine in 0.688 ml of carbon tetrachloride. The product was purified by chromatography over silica gel, eluting with ethyl acetate/hexane mixtures.

$\nu_{max}$ (CDCl$_3$) 1785.

$\delta$(CDCl$_3$) 1.07, 1.13 (9H, 2s), 1.40 (3H, m), 1.5 (1H, b), 3.50 (1H, dd,), 4.06–4.60 (1H, m) 5.40 (2H, s,), 6.25 (1H, d, J=4 Hz), 7.00–8.5 (8H, m).

EXAMPLE 71

4-Nitrobenzyl 5(R)-3-(2-cyanophenoxy)-6(S)-{1(R)-hydroxyethyl}-7-oxo-4-thia-1-azabicyclo[3,2,0]hept-2-ene-2-carboxylate 80 mg of the above compound were obtained by a procedure analogous to that described in Example 19 using 130 mg of the product of Example 70 and 18 mg of imidazole.

$\nu_{max}$ (CH$_3$Cl$_3$) 1792 cm$^{-1}$.

$\delta$(CDCl$_3$) 1.30 (3H, d), 3.71 (1H dd J=1.5 Hz and J=6 Hz), 4.00–4.30 (1H, m), 5.20 (2H, q), 5.65 (1H, d, J=1.5 Hz), 6.90–8.10 (8H, m,).

EXAMPLE 72

Potassium 5(R)-3-(2-cyanophenoxy)-6(S)-{1(R)-hydroxyethyl}-7-oxo-4-thia-1-azabicyclo[3,2,0]hept-2-ene-carboxylate 62 mg of the above compound were obtained from 80 mg of the corresponding 4-nitrobenzylcarboxylate (see Example 71) by a procedure analogous to that described in Example 21, using 17.1 mg of potassium bicarbonate.

EXAMPLE 73

4-Nitrobenzyl 3-(3-acetoxyphenoxy)-2-[4(R)-ethylthio-3(S)-{1(R)-dimethyl-(2-methylprop-2-yl)silyloxyethyl}azetidin-2-on-1-yl]-3-trimethylacetylthiopropenate 1.05 g of the above compound were obtained by a procedure analogous to that described in Example 16 using 1 g of 4-nitrobenzyl 2-[3(S)-{1(R)-dimethyl-(2-methylprop-2-yl)silyloxyethyl}-4(R)-ethylthioazetidin-2-on-1-yl]acetate, 1,34 ml of hexamethyldisilazane, 0.98 g of 3-acetoxyphenyl chlorothionoformate, 6.38 mmol of n-butyllithium and 0.53 ml of trimethylacetylchloride.

$\nu_{max}$ (CDCl$_3$) 1760 cm$^{-1}$.

$\delta$(CDCl$_3$) 0.06 (6H, s), 0.80, 0.90 (9H, 2s), 1.05, 1.10 (9H, 2s), 1.22 (3H, t, J=7 Hz), 1.25 (3H d J=6 Hz), 2.28 (3H, s), 2.70 (2H, q), 3.30 (1H, dd), 4.10–4.5 (1H, m) 5.36 (3H, bs), 6.75–8.40 (8H, m).

EXAMPLE 74

4-Nitrobenzyl 3-(3-acetoxyphenoxy)-2-[4(R)-ethylthio-3S-{1(R)-hydroxyethyl}-azetidin-2-on-1-yl]-3-trimethylthiopropenate(I) and 4-nitrobenzyl 2-[4(R)-ethylthio-3(S)-{1R-hydroxyethyl}azetidin-2-on-1-yl]-3-(3-hydroxyphenoxy)-3-trimethyl acetylthiopropenate (II)

88 mg of compound I above, and 110 mg of compound II were obtained from 400 g of the corresponding {1(R)-dimethyl-(2-methylprop-2-yl)silyloxyethyl} compound (see Example 73) by a procedure analogous to that described in Example 17 using 1 ml of concentrated hydrochloric acid, 1 ml of water and 10 ml of tetrahydrofuran. Compounds I and II were separated by column chromatography on silica gel, eluting with ethyl acetate/hexane mixtures.

data for compound (I)

$\nu_{max}$ (CDCl$_3$) 1767 cm$^{-1}$.

$\delta$(CDCl$_3$) 1.07, 1.13 (9H, 2s), 1.30 (3H, t J=7 Hz), 1.32 (3H, d J=6 Hz), 2.25 (1H bs), 2.32 (3H, s), 2.70 (2H, q), 3.28 (1H, dd), 3.90–4.40 (1H, m), 5.30 (3H, bs), 6.80–8.30 (8H, m).

data for compound (II)

$\nu_{max}$ (CDCl$_3$) 1755 cm$^{-1}$.

$\delta$(CDCl$_3$) 1.05, 1.12 (9H, 2s), 1.29 (3H, t, J=7 Hz), 1.32 (3H, d, J=6 Hz), 2.72 (2H, q), 2.85 (1H, bs), 3.28 (1H, dd), 3.95–4.50 (1H, m) 5.35 (3H, bs), 6.40–8.30 (8H, m).

EXAMPLE 75

4-Nitrobenzyl 3-(3-acetoxyphenoxy)-2-[4(S)-chloro-3(S)-{1R-hydroxyethyl}-azetidin-2-on-1-yl]-3-trimethylacetylthiopropenate 246 mg of the above compound were obtained by a process analogous to that described in Example 26 using 388 mg of the 3-(3-acetoxyphenoxy)-1(R)-hydroxyethylazetidinone derivative I defined in Example 74 and a solution of 0.72 mmol of chlorine in 1.49 ml of carbon tetrachloride. The product was purified by column chromatography. on silica gel, eluting with ethyl acetate/hexane mixtures.

$\nu_{max}$ (CDCl$_3$) 1775.

$\delta$(CDCl$_3$) 107, 1.13 (9H, 2s), 1.35 (3H, d), 2.25 (3H, s), 2.55 (1H, bs), 3.50 (1H, 2.dd), 4.00–4.60 (1H, m) 5.30 (2H, s), 6.15 (1H, 2d J=4 Hz), 6.80–8.30 (8H, m).

EXAMPLE 76

4-Nitrobenzyl 5(R)-3-(3-acetoxyphenoxy)-6(S)-{1(R)-hydroxyethyl}-7-oxo-4-thia-1-azabicyclo[3,2,0]hept-2-ene-2-carboxylate 115 mg of the above compound were obtained by a procedure analogous to that described in Example 19 using 240 mg of the chloroazetidinone derivative defined in Example 75 and 31.6 mg of imidazole.

$\nu_{max}$ (CDCl$_3$) 1782 cm$^{-1}$, 1791 (sh) cm$^{-1}$.

δ(CDCl$_3$) 1.30 (3H, d), 2.25 (3H, s), 2.60 (1H, bs), 3.71 (1H, dd J=1.5 Hz and 6 Hz), 3.90–4.40 (1H, m), 5.27 (2H, q), 5.60 (1H, d J=1.5 Hz), 6.80–8.20 (8H, m).

EXAMPLE 77

Potassium 5(R)-3-(3-acetoxyphenoxy)-6(S)-{(1R)-hydroxyethyl}-7-oxo-4-thia-1-azabicyclo[3,2,0]hept-2-ene-2-carboxylate 32 mg of the above compound were obtained from 115 mg of the corresponding 4-nitrobenzyl carboxylate (see Example 76) by a procedure analogous to that described in Example 21, using 23 mg of potassium bicarbonate.

EXAMPLE 78

4-Nitrobenzyl 2-[4(S)-chloro-3(S)-{1R-hydroxyethyl}azetidin-2-on-1-yl]-3-(3-hydroxyphenoxy)-3-trimethylacetylthio-propenate 270 mg of the above compound were obtained by a process analogous to that described in Example 26 using 400 mg of the 3-(3-hydroxyphenoxy)-1(R)-hydroxyethylazetidinone derivative II defined in Example 74 and a solution of 0.76 m mol of chlorine in 1.6 ml of carbon tetrachloride. The product was purified by chromatography on silica gel, eluting with ethyl acetate/hexane mixtures.

$\nu_{max}$ (CDCl$_3$) 1778 cm$^{-1}$.

δ(CDCl$_3$) 1.01, 1.05 (9H, 2s), 1.35 (3H, d), 2.60 (1H vbs), 3.50 (1H, d,d), 4.00–4.50 (1H, m), 5.30 (2H, s), 6.10 (1H, 2d J=4 Hz), 6.40–8.30 (8H, m).

EXAMPLE 79

4-Nitrobenzyl 5(R), 6(S)-{1(R)-hydroxyethyl}-3-(3-hydroxyphenoxy)-7-oxo-4-thia-1-azabicyclo[3,2,0]hept-2-en-2-carboxylate 150 mg of the above compound were obtained by a procedure analogous to that described in Example 19 using 265 mg of the chloroazetidinone derivative defined in Example 78 and 37.4 mg of imidazole.

$\nu_{max}$ (CDCl$_3$) 1780 cm$^{-1}$, 1790 (Sh) cm$^{-1}$.

δ(CDCl$_3$) 1.32 (3H, d), 3.10 (1H bs), 3.80 (1H, dd, J=1.5 Hz, and 6 Hz), 4.00–4.40 (1H, m), 5.30 (2H q), 5.70 (1H d J=1.5 Hz), 6.40–8.20 (8H m), 8.70 (1H bs).

EXAMPLE 80

Potassium 5(R), 6(S)-{1(R)-hydroxyethyl}-3-(3-hydroxyphenoxy)-7-oxo-4-thia-azabicyclo[3,2,0]hept-2-ene-2-carboxylate 55 mg of the above compound were obtained from 98 mg of the corresponding 4-nitrobenzyl carboxylate (see Example 79) by a procedure analogous to that described in Example 21, using 21.3 mg of potassium bicarbonate.

EXAMPLE 81

4-Nitrobenzyl 3-(4-dimethylaminosulphonylphenoxy)-2-[4(R)-ethylthio-3S-{1(R)-dimethyl-(2-methylprop-2-yl)silyloxyethyl}azetidin-2-on-1-yl]-3-trimethylacetylthiopropenate 0.93 g of the above compound was obtained by a procedure analogous to that described in Example 16, using 1.3 g of the azetidinone starting material defined in Example 16, 1.45 ml of hexamethyldisilazane, 1 g of 4-dimethylaminosulphonylphenyl chlorothionoformate, 6.88 mmol of n-butyllithium, and 0.68 ml of trimethylacetylchloride.

δCDCl$_3$0.70 (6H, s), 0.81, 0.90 (9H, 2s), 1.07, 1.15 (9H, 2s), 1.20 (3H, t, J=7 Hz), 1.30 (3H d J=6 Hz), 2.75 (6H s), 3.27 (1H dd, J=2 Hz and 4 Hz), 4.3 (1H, m), 5.3 (3H, m), 7.2–8.35 (8H, m).

EXAMPLE 82

4-Nitrobenzyl 3-(4-dimethylaminosulphonylphenoxy)-2-[4(R)-ethylthio-3(S)-{1R-hydroxyethyl}azetidin-2-on-1-yl]-3-trimethylacetylthio propenate 0.57 g of the above compound was obtained from 0.930 g of the corresponding {1(R)-dimethyl-(2-methylprop-2-yl)silyloxyethyl} compound (see Example 81) by a procedure analogous to that described in Example 17 using 1.3 ml of concentrated hydrochloric acid, 1.25 ml of water and 0.5 ml of tetrahydrofuran.

$\nu_{max}$ (CDCl$_3$) 1728, 1761 cm$^{-1}$.

δ(CDCl$_3$) 1.02, 1.11 (9H, 2s), 1.20 (3H, t), 1.25 (3H, d), 2.52 (1H, bs), 2.68 (6H, s), 2.80 (2H, q), 3.24 (1H, dd), 4.0–4.40 (1H, m), 5.30 (3H bs), 7.10–8.30 (8H m), 4.10–4.50 (1H, m), 5.35 (3H, bs), 7.1–8.4 (8H, m).

EXAMPLE 83

4-Nitrobenzyl 2-[4(S)-chloro-3(S)-{1(R)-hydroxyethyl}azetidin-2-on-1-yl]-3-(4-dimethylaminosulphonylphenoxy)-3-trimethylacetylthio-propenate 445 mg of the above compound were obtained by a process analogous to that described in Example 26 using 560 mg of the 1(R)-hydroxyethylazetidinone derivative defined in Example 82 and 1 ml of a 0.85 molar solution of chlorine in carbon tetrachloride. The product was purified by chromatography over silica gel, eluting with ethyl acetate/hexane mixtures.

$\nu_{max}$ (CDCl$_3$) 1783, 1730 cm$^{-1}$.

δ(CDCl$_3$) 1.07, 1.12 (9H, 2s), 1.40 (3H, d) 2.50 (1H, bs), 2.75 (6H, s) 3.60 (1H, m) 4.05–4.50 (1H, m) 5.35 (2H, s), 6.2 (1H, d, J=4 Hz) 7.1–8.3 (8H, m).

EXAMPLE 84

4-Nitrobenzyl 5(R)-3-(4-dimethylaminosulphonylphenoxy)-6(S)-{1(R)-hydroxyethyl}-7-oxo-4-thia-1-azabicyclo[3,2,0-]hept-2-ene-2-carboxylate 225 mg of the above compound were obtained by a procedure analogous to that described in Example 19 using 445 mg of the chloroazetidinone derivative defined in Example 83 and 50 mg of imidazole.

$\nu_{max}$ (CDCl$_3$) 1789, 1793 (sh) cm$^{-1}$.

δ(CDCl$_3$) 1.35 (3H, d, J=6 Hz) 2.60 (1H, bs), 2.83 (6H, s), 3.80 (1H dd J=1.5 Hz and J=6 Hz), 4.00–4.40 (1H, m), 5.30 (2H, q, 2H, AB, J$_{gem}$ 14 Hz), 5.73 (1H, d, J=1.5 Hz), 7.2–8.3 (8H, m).

EXAMPLE 85

Potassium 5(R)-3-(4-dimethylaminosulphonylphenoxy)-6(S)-{1(R)-hydroxyethyl}-7-oxo-4-thia-1-azabicyclo[3,2,0-]hept-2-ene-2-carboxylate 70.8 mg of the above compound were obtained from 112 mg of the corresponding 4-nitrobenzyl carboxylate (see Example 84) by a procedure analogous to that described in Example 21, using 20.4 mg of potassium bicarbonate.

EXAMPLE 86

4-Nitrobenzyl 2-[3(S)-{1(R)-dimethyl-(2-methylprop-2-yl)silyloxyethyl}-4(R)-ethylthioazetidin-2-on-1-yl]-3-(3-nitrophenoxy)-3-trimethylacetylthio-propenoate 170 mg of the above compound were obtained, as a yellow oil, by a procedure analogous to that described in Example 16, using 2.0 g of the azetidinone starting material defined in Example 16, 1.3 g of 3-nitrophenyl chlorothionoformate, 2.2 ml of hexamethyldisilazane and 10.1 mmol of n-butyllithium, and 1.5 ml of trimethylacetyl chloride.

$\nu_{max}$ (CDCl$_3$) 1730, 1765 cm$^{-1}$.

$\delta$(CDCl$_3$) 0.06 (6H, s), 0.80, 0.85 (9H, 2s), 1.00 (9H, s), 1.10–1.30 (6H, m), 2.64 (2H, q, J=7Hz), 3.19 (1H, m), 4.00–4.45 (1H, m), 5.25 (3H, bs), 7.00–8.10 (8H, m).

EXAMPLE 87

4-Nitrobenzyl 2-[3(S)-{1(R)-hydroxyethyl}-4(R)-ethylthioazetidin-2-on-1-yl]-3-(3-nitrophenoxy)-3-trimethylacetylthiopropenoate 0.755 g of the above compound was obtained from 1.7 g of the corresponding {1(R)-dimethyl-(2-methylpro-2-yl)silyloxyethyl} compound (see Example 86) by a procedure analogous to that described in Example 17, using 1.7 ml of water and 1.7 ml of concentrated hydrochloric acid.

$\nu_{max}$ (CDCl$_3$) 1730, 1762 cm$^{-1}$.

$\delta$(CDCl$_3$) 1.06, 1.16(9H, 2s), 1.20–1.38 (6H, m), 3.75 (2H, q, J=7 Hz), 3.29 (1H, dd, J=2 Hz and 4 Hz), 3.98–4.40 (1H, m), 5.27, 5.30 (3H, 2 bs), 7.25–8.18 (8H, m),

EXAMPLE 88

4-Nitrobenzyl 2-[3(S)-{1(R)-hydroxyethyl}-4(S)-chloroazetidin-2-on-1-yl]-3-(3-nitrophenoxy)-3-trimethylacetylthiopropenoate To a stirred solution of 0.755 g of the 1(R)-hydroxyethylazetidinone derivative defined in Example 87 in CDCl$_3$ at −40° C. was added a solution of 1.3 mmol of chlorine in carbon tetrachloride and the solution was stirred for 1 hour. The reaction mixture was warmed to room temperature and evaporated to dryness. Chromatography over silica gel and elution with hexane/ethyl acetate mixtures afforded 0.536 g of the title compound.

$\nu_{max}$ (CDCl$_3$) 1729, 1784 cm$^{-1}$.

$\delta$(CDCl$_3$) 1.02, 1.08 (9H, 2s), 1.15 (3H, d, J=6 Hz), 2.45 (1H, bs), 3.56 (1H, dd, J=4 Hz and 9 Hz), 3.90–4.57 (1H, m), 5.34 (2H, s), 6.16 (1H, d, J=4 Hz), 7.40–8.33 (8H, m).

EXAMPLE 89

4-Nitrobenzyl 5(R),6(S)-{1(R)-hydroxyethyl}-3-(3-nitrophenoxy)-7-oxo-4-thia-1-azabicyclo[3,2,0]hept-2-en-2-carboxylate 0.176 g of the above compound was obtained by a procedure analogous to that described in Example 19 using 0.299 g of the 4(S)-chloroazetidinone of Example 88 and 0.0668 g of imidazole.

$\nu_{max}$ (CDCl$_3$) 1712, 1789 cm$^{-1}$.

$\delta$(CDCl$_3$) 1.32 (3H, d, J=6 Hz), 2.20 (1H, bs), 3.80–3.90 (1H, m), 4.10–4.40 (1H, m), 5.33 (2H, q), 5.72 (1H, d, J=1.5 Hz), 7.48–8.25 (8H, m).

EXAMPLE 90

4-Nitrobenzyl 5(R),3-(3-aminophenoxy)-6(S)-{1(R)-hydroxyethyl}-7-oxo-4-thia-1-azabicyclo[3,2,0]hept-2-en-2-carboxylate A mixture of a solution of 0.175 g of 4-nitrobenzyl 5(R),6(S)-{1(R)-hydroxyethyl}-3-(3-nitrophenoxy)-7-oxo-4-thia-1-azabicyclo[3,2,0]hept-2-en-2-carboxylate in ethyl acetate and 25 mg of Adams catalyst (platinum dioxide) was hydrogenated at 50 p.s.i. for 105 mins. The mixture was filtered through Celite (Trade Mark) and evaporated to dryness. Chromatography over silica gel and elution with hexane/ethyl acetate mixtures afforded 75 mg of the title compound, as a yellow solid.

$\nu_{max}$ (CDCl$_3$) 1778 cm$^{-1}$.

$\delta$((CD$_3$)$_2$CO) 1.30 (3H, m), 3.70–3.85 (1H, m), 3.98–4.40 (1H, m), 5.32 (2H, q), 5.70 (1H, d, J=1.5 Hz), 6.55–7.30 (4H, m), 7.55–8.16 (4H, m).

EXAMPLE 91

Potassium 5(R),3-(3-aminophenoxy)-6(S)-{1(R)-hydroxyethyl}-7-oxo-4-thia-1-azabicyclo[3,2,0]hept-2-en-2-carboxylate 59 mg of the title compound were obtained by a procedure analogous to that described in Example 21 using 66 mg of 4-nitrobenzyl 5(R),3-(3-aminophenoxy)-6(S)-{1(R)-hydroxyethyl}-7-oxo-4-thia-1-azabicyclo[3,2,0-]hept-2-en-2-carboxylate and 15 mg potassium hydrogen carbonate and 10% palladium/charcoal.

EXAMPLE 92

4-Nitrobenzyl 3-[4-(cyanomethyl)phenoxy]-2[3(S)-{1(R)-dimethyl-(2-methylprop-2-yl)silyloxyethyl}-4(R)-ethylthioazetidin-2-on-yl]-3-trimethylacetylthiopropenate 326 mg of the above compound were obtained by a procedure analogous to that described in Example 16, using 0.5 g of the azetidinone starting material defined in Example 16, 1.66 ml of n-butyllithium, 0.59 ml of hexamethyldisilazane, 0.525 ml of trimethylacetyl chloride, and 0.269 g of 4-(cyanomethyl)phenyl chlorothionoformate.

$\nu_{max}$ (CDCl$_3$) 1762 cm$^{-1}$, 2240 cm$^{-1}$.

$\delta$(CDCl$_3$) 0.05 (6H, s), 0.79, 0.85 (9H, 2s), 1.03, 1.07 (9H, 2s), 1.21 (3H, t, J=7 Hz), 1.25 (3H, d, J=6 Hz), 2.60 (2H, q, J=7 Hz), 3.23 (1H, dd, J=2 Hz, 4 Hz), 3.73 (2H, s), 3.97–4.44 (1H, m), 5.25 (3H, bs), 6.85–8.25 (8H, m).

EXAMPLE 93

4-Nitrobenzyl 3-[4-(cyanomethyl)phenoxy]-2-(4(R)-ethylthio-3(S)-{1(R)-hydroxyethyl}-azetidin-2-on-1-yl]-3-trimethylacetylthiopropenate 159 mg of the above compound were obtained by a procedure analogous to that described in Example 17 using 348 mg of the corresponding {1(R)-dimethyl-(2-methylprop-2-yl)silyloxyethyl} compound (see Example 92), 0.5 ml of concentrated hydrochloric acid, and 0.5 ml of water.

$\nu_{max}$ (CDCl$_3$) = 1760, 2240 cm$^{-1}$.

$\delta$(CDCl$_3$) 1.07, 1.12 (9H, 2s), 1.28 (3H, t, J=7 Hz), 1.35 (3H, d, J=6 Hz), 2.38 (1H, bs), 2.72 (2H, q, J=7

Hz), 3.23 (1H, dd, J=2 Hz+4 Hz), 3.71 (2H, s), 3.95–4.40 (1H, m), 5.27 (3H, bs), 6.86–8.23 (8H, m).

EXAMPLE 94

4-Nitrobenzyl 2-[4(S)-chloro-3(S)-{1(R)-hydroxyethyl}-azetidin-2-on-1-yl]-3-[4-(cyanomethyl)phenoxy]-3-trimethylacetylthiopropenate 70 mg of the above compound were obtained by a process analogous to that described in Example 26 using 100 mg of the 1(R)-hydroxyethylazetidinone derivative defined in Example 93 and 0.21 ml of a 0.85 molar solution of chlorine in carbon tetrachloride. The product was purified by chromatography over silica gel, eluting with ethyl acetate/hexane mixtures.

$\nu_{max}$ (CDCl$_3$)=1780 cm$^{-1}$, 2242 cm$^{-1}$.

$\delta$(CDCl$_3$) 1.08, 1.14 (9H, 2s), 1.35 (3H, d, J=6 Hz), 2.40 (1H, bs), 3.52 (1H, dd, J=4 Hz), 3.74 (2H, s), 4.05–4.55 (1H, m), 5.32 (2H, s), 6.17 (1H, d, J=4 Hz), 6.89–8.28 (8 H, m).

EXAMPLE 95

4-Nitrobenzyl 5(R)-3-[4-cyanomethyl)phenoxy]-6(S)-{1(R)-hydroxyethyl}-7-oxo-4-thia-1-azabicyclo[3,2,0]hept-2-ene-2-carboxylate 61 mg of the above compound were obtained by a procedure analogous to that described in Example 19 using 190 mg of the chloroazetidinone derivative defined in Example 94 and 28 mg of imidazole.

$\nu_{max}$ (CDCl$_3$) 1785, 1795 (sh) and 2242 cm$^{-1}$.

$\delta$(CDCl$_3$) 1.38 (3H, d, J=6 Hz), 2.39 (1H, bs), 3.80 (3H, m), 4.05–4.43 (1H, m), 5.34 (2H, q), 5.68 (1H, d, J=1.5 Hz), 7.09–7.40 (4H, m), 7.43–8.31 (4H, m).

EXAMPLE 96

Potassium 5(R)-3-[4-(cyanomethyl)phenoxy]-6(S)-{1(R)-hydroxyethyl}-7-oxo-4-thia-1-azabicyclo[3,2,0]hept-2-ene-2-carboxylate 13 mg of the above compound were obtained from 60 mg of the corresponding 4-nitrobenzyl carboxylate (see Example 95) by a procedure analogous to that described in Example 21 using 12.5 mg of potassium bicarbonate.

EXAMPLE 97

4-Nitrobenzyl 5(R),6(S)-{1(R)-acetoxyethyl}-3-(4-fluorophenoxy)-7-oxo-4-thia-1-azabicyclo[3,2,0]hept-2-ene-2-carboxylate To a stirred solution of 100 mg of 4-nitrobenzyl 3-(4-fluorophenoxy)-6(S)-{1(R)-hydroxyethyl}-7-oxo-4-thia-1-azabicyclo[3,2,0]hept-2-ene-2-carboxylate in 3 ml of tetrahydrofuran at 0° C. was added a solution of 3 mg of dimethylaminopyridine in 0.5 ml of acetic anhydride. After 30 minutes, the reaction mixture was warmed to room temperature, partitioned between ethyl acetate and water, the organic layer was washed with saturated sodium bicarbonate solution and brine, dried over magnesium sulphate, and evaporated in vacuo to dryness. Chromatography over silica gel and elution with ethyl acetate-hexane mixtures afforded 74 mg of the title compound.

$\delta$(CDCl$_3$) 1.40 (3H, d, J=6 Hz), 2.01 (3H, s), 3.80 (1H, dd, J=1.5 Hz, 6 Hz), 4.99–5.26 (1H, m), 5.29 (2H, q), 5.51 (1H, d, J=1.5 Hz), 6.87–7.23 (4H, m), 7.34–8.22 (4H, m).

EXAMPLE 98

4-Nitrobenzyl 5(R),6(S)-{1(R)-benzoyloxyethyl}-3-(4-cyanophenoxy)-7-oxo-4-thia-1-azabicyclo[3,2,0]hept-2-ene-2-carboxylate 70 mg of the above compound were obtained from the corresponding 1(R)-hydroxyethyl compound (defined in Example 42) by a procedure analogous to that described in Example 97, using 100 mg of the 1(R)-hydroxyethyl compound, 1 ml of tetrahydrofuran, 1 mg of dimethylaminopyridine, 33 mg of benzoyl chloride and 18 mg of pyridine.

$\delta$(CDCl$_3$) 1.3 (3H, d, J=6 Hz), 3.95 (1H, dd, J=1.5 and 6 Hz), 5.25 (3H, m), 5.8 (1H, d, J=1.5 Hz), 7.0–8.2 (13H, m).

EXAMPLE 99

4-Nitrobenzyl 5(R),6(S)-{1(R)-acetoxyethyl}-3-(4-methylsulphinylphenoxy)-7-oxo-4-thia-1-azabicyclo[3,2,0]hept-2-ene-2-carboxylate 71 mg of the above compound were obtained, as an oil, from 100 mg of the corresponding 1(R)-hydroxy compound (defined in Example 20) by a procedure analogous to that described in Example 97 using 25 ul of acetic anhydride, 1 ml of tetrahydrofuran, and 2 mg of dimethylaminopyridine.

$\delta$(CDCl$_3$) 1.38 (3H, d, J=6 Hz), 2.02 (3H, s), 2.74 (3H s), 3.85 (1H, dd, J=1.5 and 6 Hz), 5.3 (3H, m), 5.8 (1H, d J=1.5 Hz), 7.0–8.3 (8H, m).

EXAMPLE 100

4-Nitrobenzyl 5(R),6(S)-{1(R)-(phenoxyacetoxy)ethyl}-3-(4-methylsulphinylphenoxy)-7-oxo-4-thia-1-azabicyclo[3,2,0-]hept-2-ene-2-carboxylate 53 mg of the above compound were obtained from 170 mg of the corresponding 1(R)-hydroxyethyl compound (see Example 20) by a procedure analogous to that described in Example 97 using 86.2 mg of phenoxyacetyl chloride, 40 mg of pyridine and 1 ml of tetrahydrofuran $\delta$(CDCl$_3$) 1.35 (3H, d J=6 Hz), 2.73 (3H, s), 3.96 (1H, dd, J=1.5 and 6 Hz), 4.4 (2H, m), 5.1 (2H, m), 5.31 (2H, m), 5.78 (1H, d, J=1.5 Hz), 7.0–8.3 (13H, m).

EXAMPLE 101

4-nitrobenzyl 5(R)-3-(2-fluorophenoxy)-6(S)-{1(R)-pivaloyloxymethyloxyethyl}-7-oxo-4-thia-1-azabicyclo[3,2,0]hept-2-ene-2-carboxylate To a stirred solution of 50 mg of the corresponding 1(R)-hydroxyethyl compound (see Example 60) and 96 mg of pivaloyloxymethyl iodide in 1 ml of tetrahydrofuran were added portionwise 125 mg of silver oxide. The crude product was filtered, was evaporated in vacuo and then chromatographed on silica gel. Elution with ethyl acetate/hexane mixtures afforded the title compound as an oil.

$\nu_{max}$ (CDCl$_3$) 1795 cm$^{-1}$.

$\delta$(CDCl$_3$) 1.20 (9H, s), 1.38 (3H, d J=6 Hz), 3.85 (1H, dd J=1.5 and 6 Hz), 4.5 (1H, m), 5.33 (2H, m), 5.80 (3H, bs), 7.15–8.25 (8H, m).

EXAMPLE 102

Potassium 5(R),6(S)-{1(R)-acetoxyethyl}-3-(4-fluorophenoxy)-7-oxo-4-thia-1-azabicyclo[3,2,0]hept-2-ene-2-carboxylate 47 mg of the above salt were obtained from 74 mg of the corresponding 4-nitrobenzyl carboxylate (see Example 97) by a procedure analogous to that described in Example 21, using 14 mg of potassium bicarbonate and 100 mg of 10% Pd on carbon.

EXAMPLE 103

Potassium 5(R),6(S)-{1(R)-acetoxyethyl}-3-(4-methylsulphinylphenoxy)-7-oxo-4-thia-1-azabicyclo[3,2,0]hept2-2ene-2-carboxylate 41 mg of the above salt were obtained by a procedure analogous to that described in Example 21 from 55 mg of the corresponding 4-nitrobenzyl carboxylate (see Example 99) using 10 mg of potassium bicarbonate and 50 mg of palladium on charcoal.

EXAMPLE 104

Potassium 3-(2-fluorophenoxy)-(5R),6(S)-{1(R)-pivaloyloxymethyloxyethyl}-7-oxo-4-thia-1-azabicyclo[3,2,0]hept-2-ene-2-carboxylate 13 mg of the above salt were obtained as a yellow, oily solid by a procedure analogous to that described in Example 21, using 15 mg of the corresponding 4-nitrobenzyl carboxylate (see Example 101) 2.6 mg of potassium bicarbonate and 20 mg of 10% palladium on charcoal.

EXAMPLE 105

Potassium 5(R),6(S)-{1(R)-benzoyloxyethyl}-3-(4-cyanophenoxy)-7-oxo-4-thia-1-azabicyclo[3,2,0]hept-2-ene-2-carboxylate 48 mg of the above salt were obtained from 65 mg of the corresponding 4-nitrobenzyl carboxylate (see Example 98) by a procedure analogous to that described in Example 21, using 11.4 mg of potassium bicarbonate.

EXAMPLE 106

Potassium 5(R),6(S)-{1(R)-(phenoxyacetoxy)ethyl}-3-(4-methylsulphinylphenoxy)-7-oxo-4-thia-1-azabicyclo[3,2,0]hept-2-ene-2-carboxylate 34 mg of the above salt were obtained from 40 mg of the corresponding 4-nitrobenzyl carboxylate (see Example 100) by a procedure analogous to that described in Example 21 using 6.3 mg of potassium bicarbonate.

EXAMPLE 107

2-Methyloxycarbonyl-3-thienyl chlorothionoformate

To a vigorously stirred solution of 20 g of methyl 3-hydroxythiophene-2-carboxylate and 15 ml of thiophosgene in alumina-dried chloroform at 0° was added dropwise a solution of 5.1 g of sodium hydroxide in 50 ml of water. The mixture was then warmed to room temperature, was stirred for a further 105 minutes, and then partitioned. The organic layer was separated, was washed with ice-cold water, with brine and thoroughly dried over $CaCl_2$. Evaporation in vacuo afforded a yellow-orange oil which solidified on standing.

$M^+$ 235.9381 and 237.9337.

Found C, 35.79; H, 2.20; O, 20.13; Cl, 14.40; S, 27.38%.

$\delta(CDCl_3)$ 3.85 (3H, s), 6.95 (1H, d J=6 Hz), 7.055 (1H, d J=6 Hz).

EXAMPLE 108

4-Nitrobenzyl 2-[3(S)-{1(R)-dimethyl(2-methylprop-2-yl)silyloxyethyl}-4(R)-ethylthio-azetidin-2-on-1-yl]-3-(2-methyloxycarbonyl-3-thienyloxy)-3-trimethylacetylthiopropenate 580 mg of the above compound were obtained by a procedure analogous to that described in Example 16, using 1 g of the azetidinone starting material, 4.90 mg of 2-methyloxycarbonyl-3-thienyl chloroformate (see Example 107), 1.18 ml of hexamethyldisilazane and 5.32 mmol of n-butyllithium, and 0.525 ml of trichloroacetyl chloride.

$\nu_{max}$ $(CDCl_3)$ 1765 cm$^{-1}$.

$\delta(CDCl_3)$ 0.06 (6H, s), 0.81, 0.87 (9H, 2s), 0.98, 1.05 (9H, 2s), 1.1–1.35 (6H, m), 2.70 (2H, q J=7 Hz), 3.23 (1H, dd J=2 Hz and 4 Hz), 3.85 (3H, s), 4.0–4.4 (1H, m), 5.3 (2H, s), 5.40 (1H, d, J=2 Hz), 6.9–8.3 (6H, m).

EXAMPLE 109

4-Nitrobenzyl 2-[4(R)-ethylthio-3(S)-{1(R)-hydroxyethyl}-azetidin-2-on-1-yl]-3-(2-methyloxycarbonyl-3-thienyloxy)-3-trimethylacetylthiopropenate 290 mg of the above compound were obtained from 570 mg of the corresponding {1(R)-dimethyl-(2-methylprop-2-yl)-silyloxyethyl} compound (see Example 108) by a procedure analogous to that described in Example 17, using 0.5 ml of water and 0.5 ml of concentrated hydrochloric acid.

$\nu_{max}$ $(CDCl_3)$ 1760 cm$^{-1}$.

$\delta(CDCl_3)$ 1.01, 1.09 (9H, 2s), 1.2–1.48 (6H, m), 2.5 (1H, bs), 2.65 (2H, q J=6 Hz), 3.25 (1H, dd J=2 Hz and 4 Hz), 3.85 (3H, s), 4.0–4.4 (1H, m), 5.3 (3H, bs), 6.9–8.27 (6H, m).

EXAMPLE 110

4-Nitrobenzyl 2-[4(S)-chloro-3(S)-{1(R)-hydroxyethyl}-azetidin-2-on-1-yl]-3-(2-methyloxycarbonyl-3-thienyloxy)-3-trimethylacetylthiopropenate 145 mg of the above compound were prepared by a procedure analogous to that described in Example 26 using 290 mg of the 4-(R)-ethylthio azetidinone derivative defined in Example 109 and 0.49 mmol of chlorine in 1.5 ml carbon tetrachloride.

$\nu_{max}$ $(CDCl_3)$ 1780 cm$^{-1}$.

$\delta(CDCl_3)$ 1.0, 1.04 (9H, 2s), 1.2–1.6 (6H, m), 2.5 (1H, bs), 3.52 (1H, dd J=4 Hz and 7 Hz), 3.85 (3H, s), 3.95–4.5 (1H, m), 5.20 (2H, s), 5.99 (1H, d J=4 Hz), 6.9–8.2 (8H, m).

EXAMPLE 111

4-Nitrobenzyl 5-(R),6(S)-{1(R)-hydroxyethyl}-3-(2-methyloxycarbonyl-3-thienyloxy)-7-oxo-4-thia-1-azabicyclo[3,2,0]hept-2-ene-2-carboxylate 68 mg of the above compound were obtained by a procedure analogous to that described in Example 19 using 145 mg of the product of Example 110 and 16 mg of imidazole.

$\nu_{max}$ (CDCl$_3$) 1793 cm$^{-1}$.

$\delta$(CDCl$_3$) 1.37 (3H, d, J=6 Hz), 2.2 (1H, bs), 3.7 (4H, m), 4.01–4.5 (1H, m), 5.34 (2H, q), 5.62 (1H, d, J=1.5 Hz), 6.9–8.2 (6H, m).

EXAMPLE 112

Potassium 5(R),6(S)-{1(R)-hydroxyethyl}-3-(2-methyloxycarbonyl-3-thienyloxy)-7-oxo-4-thia-1-azabicyclo[3,2,0]hept-2-ene-2-carboxylate 49 mg of the above compound were obtained by a procedure analogous to that described in Example 21, using 60 mg of the corresponding 4-nitrobenzyl carboxylate (see example 111) and 11.8 mg of potassium bicarbonate.

We claim:

1. A compound of formula III

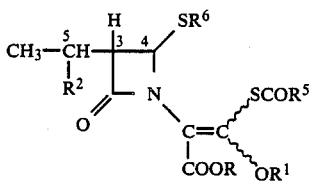

wherein R is hydrogen or a carboxyl esterifying group removable by hydrolysis, by photolysis, by reduction, or by enzyme action to give the free acid, R$^1$ is phenyl, naphthyl, thieny, pyridyl, quinolyl or isoquinolyl being unsubstituted or substituted by one, two or three substituents, which may be the same or different, selected from the group consisting of halogen atoms and —OH, —NH$_2$, —NO$_2$, —CN, —N$_3$, R$^3$—, R$^3$O—, R$^3$S—, R$^3$—SO—, R$^3$—SO$_2$—, R$^3$—CO—, R$^3$O—CO—, R$^3$—CO—O—, H$_2$N—CO—,

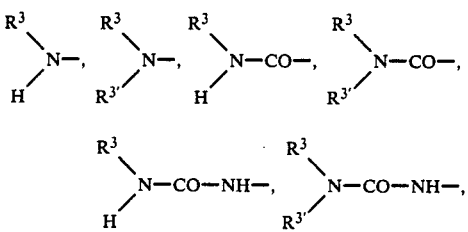

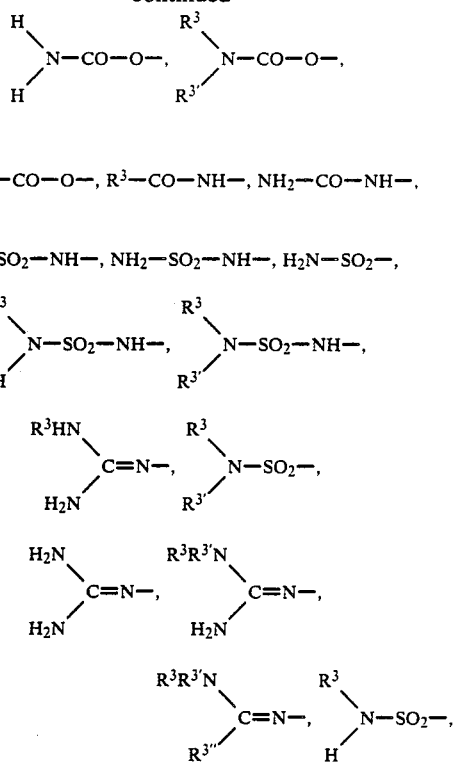

—CF$_3$, —SCF$_3$, —SOCF$_3$, —SO$_2$CF$_3$ and HO—CO— groups, in which R$^3$, R$^3\prime$ and R$^3\prime\prime$ are each an alkyl group having from 1 to 4 carbon atoms, R$^3$, R$^3\prime$ and R$^3\prime\prime$ being the same or different, R$^2$ is hydrogen, or a hydroxyl group which may be protected by a hydroxyl reaction-protecting group selected from the group consisting of R$^{10}$CO— or R$^{11}$— in which R$^{10}$ is hydrogen or a straight or branched chain alkyl group having from 1 to 4 carbon atoms, phenyl, or phenoxyalkyl wherein the alkyl group has from 1 to 4 carbon atoms and R$^{11}$ is an alkanoyloxymethyl group having from 1 to 4 carbon atoms in the alkanoyl moiety, R$^5$ is an alkyl group having from 1 to 4 carbon atoms or a phenyl group, R$^6$ is an alkyl group having from 1 to 8 carbon atoms, an alkenyl group having from 3 to 8 carbon atoms, or a phenyl group.

2. A compound as claimed in claim 1 wherein R$^2$ is hydroxyl or protected hydroxyl and the stereochemistry at carbon atom No. 5 is (R).

3. A compound as claimed in claim 1 wherein R$^2$ is hydroxyl and the stereochemistry at carbon atom No. 4 is (R).

4. A compound as claimed in claim 1 wherein R$^2$ is hydroxyl or protected hydroxyl and the stereochemistry at carbon atom No. 3 is (S).

5. A compound as claimed in claim 1 wherein R$^2$ is hydroxyl and the stereochemistry at carbon atom Nos. 3, 4 and 5 is (S), (R) and (R), respectively.

* * * * *